United States Patent
Sachs et al.

(10) Patent No.: US 10,832,795 B2
(45) Date of Patent: Nov. 10, 2020

(54) COMPRESSED SENSING FOR SIMULTANEOUS MEASUREMENT OF MULTIPLE DIFFERENT BIOLOGICAL MOLECULE TYPES IN A SAMPLE

(71) Applicant: The Board of Trustees of the Leland Standford Junior University, Palo Alto, CA (US)

(72) Inventors: Karen Sachs, Palo Alto, CA (US); Mohammed N. AlQuraishi, Cambridge, MA (US); Solomon Itani, Vallejo, CA (US); Garry P. Nolan, Menlo Park, CA (US); Sean C. Bendall, San Mateo, CA (US); Tyler J. Burns, Stanford, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 512 days.

(21) Appl. No.: 15/466,329

(22) Filed: Mar. 22, 2017

(65) Prior Publication Data
US 2018/0150596 A1 May 31, 2018

Related U.S. Application Data

(63) Continuation of application No. 13/834,260, filed on Mar. 15, 2013, now abandoned.

(60) Provisional application No. 61/714,129, filed on Oct. 15, 2012.

(51) Int. Cl.
*G16B 20/00* (2019.01)
*G01N 33/49* (2006.01)
*G01N 15/14* (2006.01)

(52) U.S. Cl.
CPC ............. *G16B 20/00* (2019.02); *G01N 15/14* (2013.01); *G01N 15/1425* (2013.01); *G01N 33/4915* (2013.01)

(58) Field of Classification Search
None
See application file for complete search history.

(56) References Cited

U.S. PATENT DOCUMENTS 7,198,900 B2 * 4/2007 Woudenberg ........ C12Q 1/6827
506/4
2012/0244631 A1 9/2012 McAdams

OTHER PUBLICATIONS

A Abdelrahman, et al., "Lanthanide-Containing Polymer Microspheres by Multiple-Stage Dispersion Polymerization for Highly Multiplexed Bioassays", "Journal of American Chemical Society", 2009, pp. 15276-15283, vol. 131, No. 42, Publisher: American Cancer Society, Published in: http://pubs.acs.org/doi/abs/10.1021/ja9052009#citing.
A Abdelrahman, et al., "Metal-Containing Polystyrene Beads as Standards for Mass Cytometry", "Journal of Analytical Atomic Spectrometry", 2010, pp. 260-268, vol. 25, No. 3, Publisher: Royal Society of Chemistry, Published in: http://pubs.rsc.org/en/Content/ArticleLanding/2010/JA/b921770c.
D Bandura, et al., "Mass Cytometry: Technique for Real Time Single Cell Multitarget Immunoassay Based on Inductively Coupled Plasma Time-of-", "Analytical Chemistry", 2009, pp. 6813-6822, vol. 81, No. 16, Publisher: American Chemistry Society, Published in: http://pubs.acs.org/doi/abs/10.1021/ac901049w?journalCode=ancham.
S Bendall, et al., "Single-Cell Mass Cytometry of Differential Immune and Drug Responses Across a Human Hematopoietic Continuum", "Science", May 6, 2011, pp. 687-696, vol. 332, No. 6030, Publisher: American Association for the Advancement of Science, Published in: http://www.sciencemag.org/content/332/6030/687.short.
E. J. Candes and J. Romberg, "Quantitative robust uncertainty principles and optimally sparse decompositions", "Foundations of Computational Mathematics", 2006, pp. 227-254, vol. 6, No. 2, Publisher: Springer, Published in: http://www.springer.com/mathematics/computational+science+%26+engineering/journal/10208.
E. Candes and T. Tao, "The Dantzig selector: Statistical estimation when p is much larger than n", "Annals of Statistics", 2007, pp. 2313-2351, vol. 35, No. 6, Publisher: Institute of Mathematical Statistics, Published in: http://projecteuclid.org/DPubS/Repository/1.0/Disseminate?handle=euclid.aos/1201012958&view=body&content-type=pdfview_1.
E. J. Candes and B. Recht, "Exact matrix completion via convex optimization", "Foundations of Computational Mathematics", 2008, pp. 717-772, vol. 9, Publisher: Springer, Published in: http://www.springer.com/mathematics/computational+science+%26+engineering/journal/10208.
E Candes and M Wakin, "An Introduction to Compressive Sampling", "Signal Processing Magazine", Mar. 2008, pp. 21-30, vol. 25, No. 2, Publisher: Institute of Electrical and Electronics Engineers, Published in: http://ieeexplore.ieee.org/xpl/login.jsp?tp=&arnumber=4472240&url=http%3A%2F%2Fieeexplore.ieee.org%2Fxpls%2Fabs_all.jsp%3Farnumber%3D4472240.
E Candes and Y Plan, "A Probabilistic and RIPless Theory of Compressed Sensing", "IEEE Transactions on Information Theory", Nov. 2010, Publisher: Institute of Electrical and Electronics Engineers, Published in: http://arxiv.org/abs/1011.3854, 36 pages.
J. Friedman, T. Hastie, et al., "Regularization Paths for Generalized Linear Models via Coordinate Descent", "Journal of Statistical Software", 2010, pp. 1-22, vol. 33, No. 1, Publisher: American Statistical Association, Published in: http://www.jstatsoft.org/v33/i01.

(Continued)

*Primary Examiner* — Lori A. Clow
(74) *Attorney, Agent, or Firm* — Wolter Van Dyke Davis, PLLC; Eugene J. Molinelli

(57) ABSTRACT

A method and apparatus for simultaneously determining multiple different biological molecule types in a sample include labeling each different biological molecule type in a biological sample with a unique combination of a plurality of labels. Each different biological molecule type is selected from a population of M different biological molecules types. The plurality of labels is selected from a population of L different labels; and, M is greater than L. Measurements are obtained of relative abundances of the L different labels in the sample. Relative abundance of up to M different biological molecule types in the sample are determined based on the measurements and a method of compressed sensing.

23 Claims, 21 Drawing Sheets

(56) References Cited

OTHER PUBLICATIONS

G. M. James and P. Radchenko, "A generalized Dantzig selector with shrinkage tuning", "Biometrika", 2009, pp. 323-337, vol. 96, No. 2, Publisher: Biometrika Trust, Published in: http://biomet.oxfordjournals.org/content/96/2/323.full.pdf+html.

P Krutzik and G Nolan, "Intracellular Phospho-protein Staining Techniques for Flow Cytometry: Monitoring Single Cell Signaling Events", "Cytometry", Oct. 2003, pp. 61-70, vol. 55A, No. 2, Publisher: Wiley-Liss Inc., Published in: http://onlinelibrary.wiley.com/doi/10.1002/cyto.a.10072/abstract; jsessionid=E36BE0E9FC4DBDE405DB8E3726FFD9CB.d03t04.

R. Tibshirani, "Regression shrinkage and selection via the Lasso", "Journal of the Royal Statistical Society, Series B (Methodological)", 1996, pp. 267-288, vol. 58, No. 1, Publisher: Royal Statistical Society, Published in: http://links:jstor.org/sici?sici=0035-9246%281996%2958%3A1%3C267%3ARSASVT%3E2.0.CO%3B2-G.

J. A. Tropp, "On the conditioning of random subdictionaries", "Applied and Computational Harmonic Analysis", 2008, pp. 1-24, vol. 25, No. 1, Publisher: Elsevier, Published in: Amsterdam.

Bendall, et al. "A deep profiler's guide to cytometry", "Trends in Immunology", 2012, pp. 323-332, vol. 33.

Pyne, et al. "Automated high-dimensional flow cytometric data analysis", "PNAS", 2009, pp. 8519-8524, vol. 106.

Qiu, et al. "Extracting a cellular hierarchy from high-dimensional cytometry data with SPADE", "Nature Biotech", 2011, pp. 886-893, vol. 29.

Roederer, et al. "SPICE: Exploration and analysis of post-cytometric complex multivariate datasets", "Cytometry A.", 2011, pp. 167-174, vol. 79.

Walther, et al. "Automatic Clustering of flow cytometry data with density-based merging", "Advances in Bioinformatics", 2009, pp. 1-7.

Zare, et al. "Data reduction for spectral clustering to analyze high throughput flow cytometry data", "BMC Bioinformatics", 2010, pp. 1-16, vol. 11.

\* cited by examiner

FIG. 2

|  | $C_1$ | $C_2$ | $C_3$ | ... |  | $C_{31}$ |
|---|---|---|---|---|---|---|
| $Protein_1$ | 1 | 0 | 0 | 1 | 1 | 1 |
| . | 0 | 1 | 0 | 1 | 0 | 0 |
| . | 1 | 0 | 1 | 0 | 1 | 0 |
| . | 1 | 0 | 0 | 1 | 0 | 1 |
| . | 0 | 0 | 1 | 0 | 1 | 0 |
| $Protein_{80}$ | 0 | 1 | 1 | 0 | 0 | 1 |

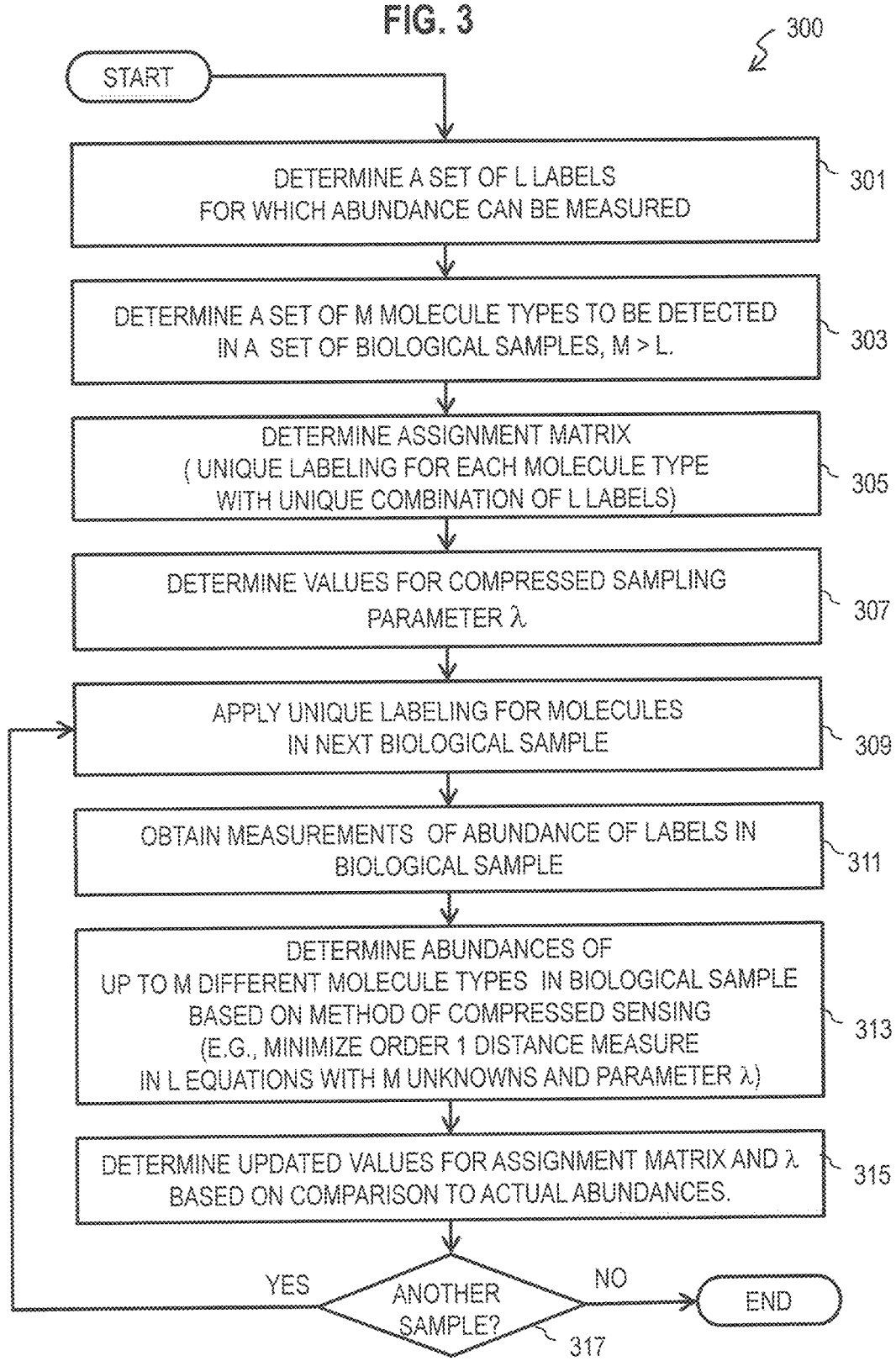

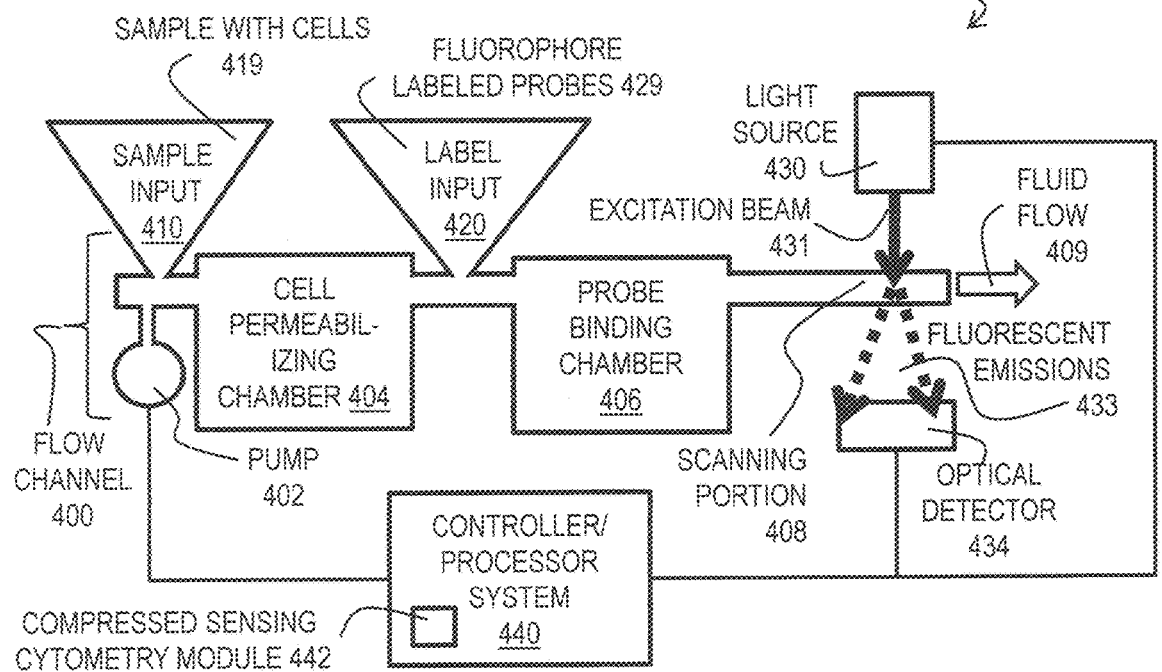
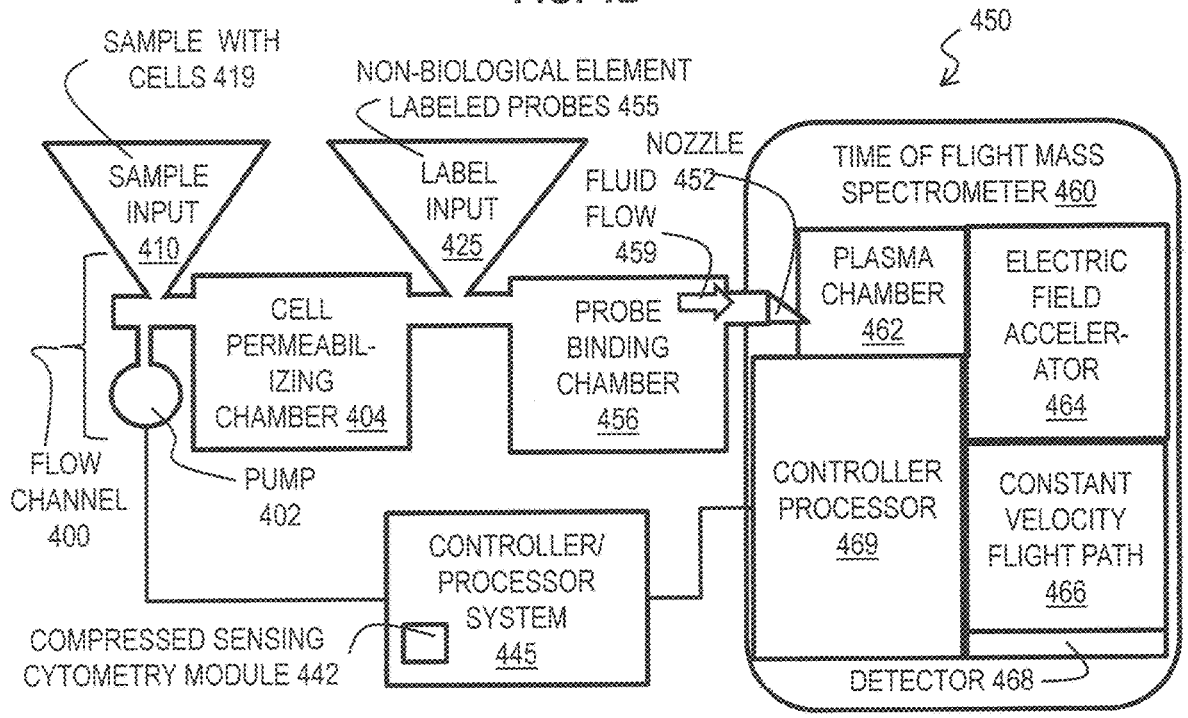

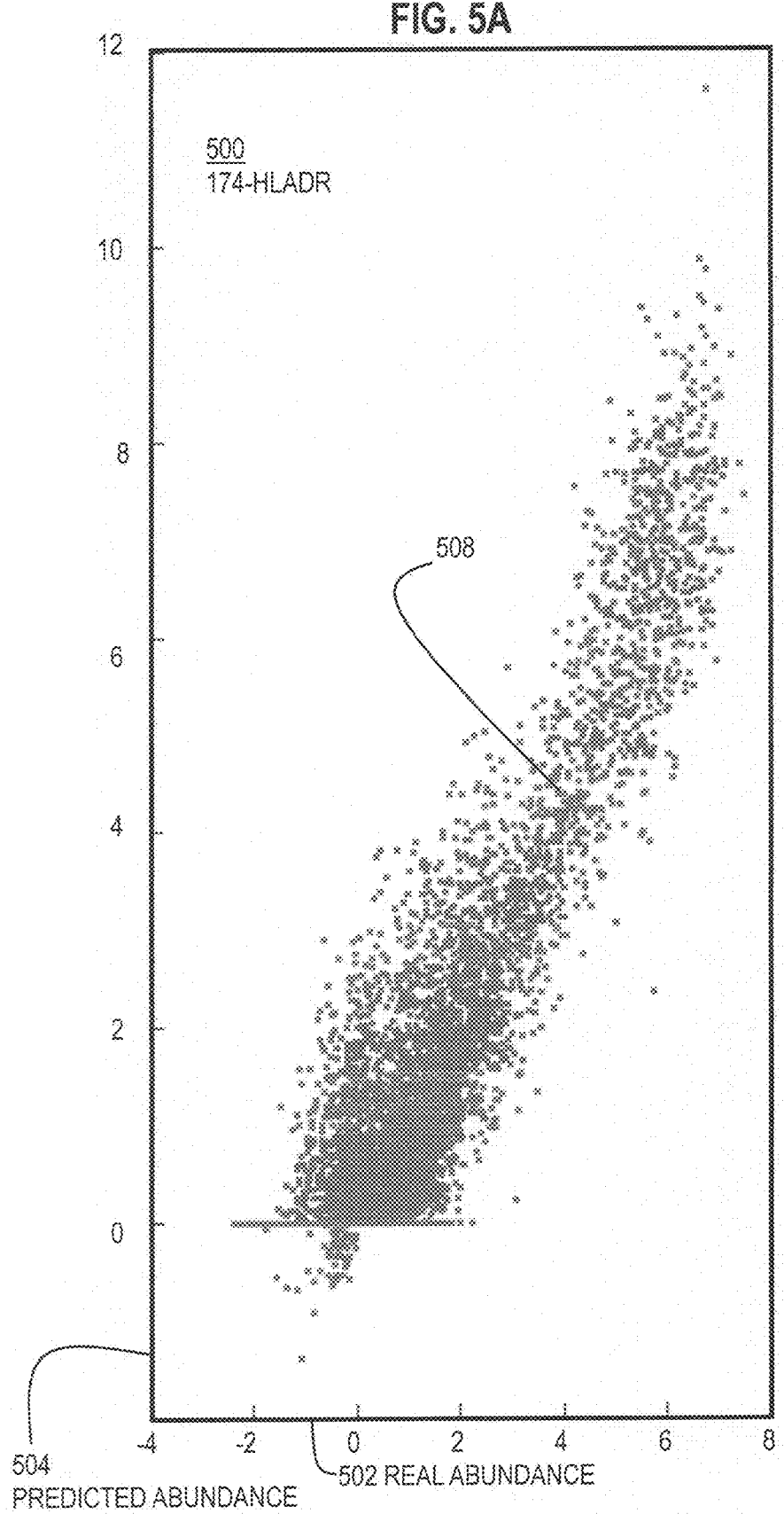

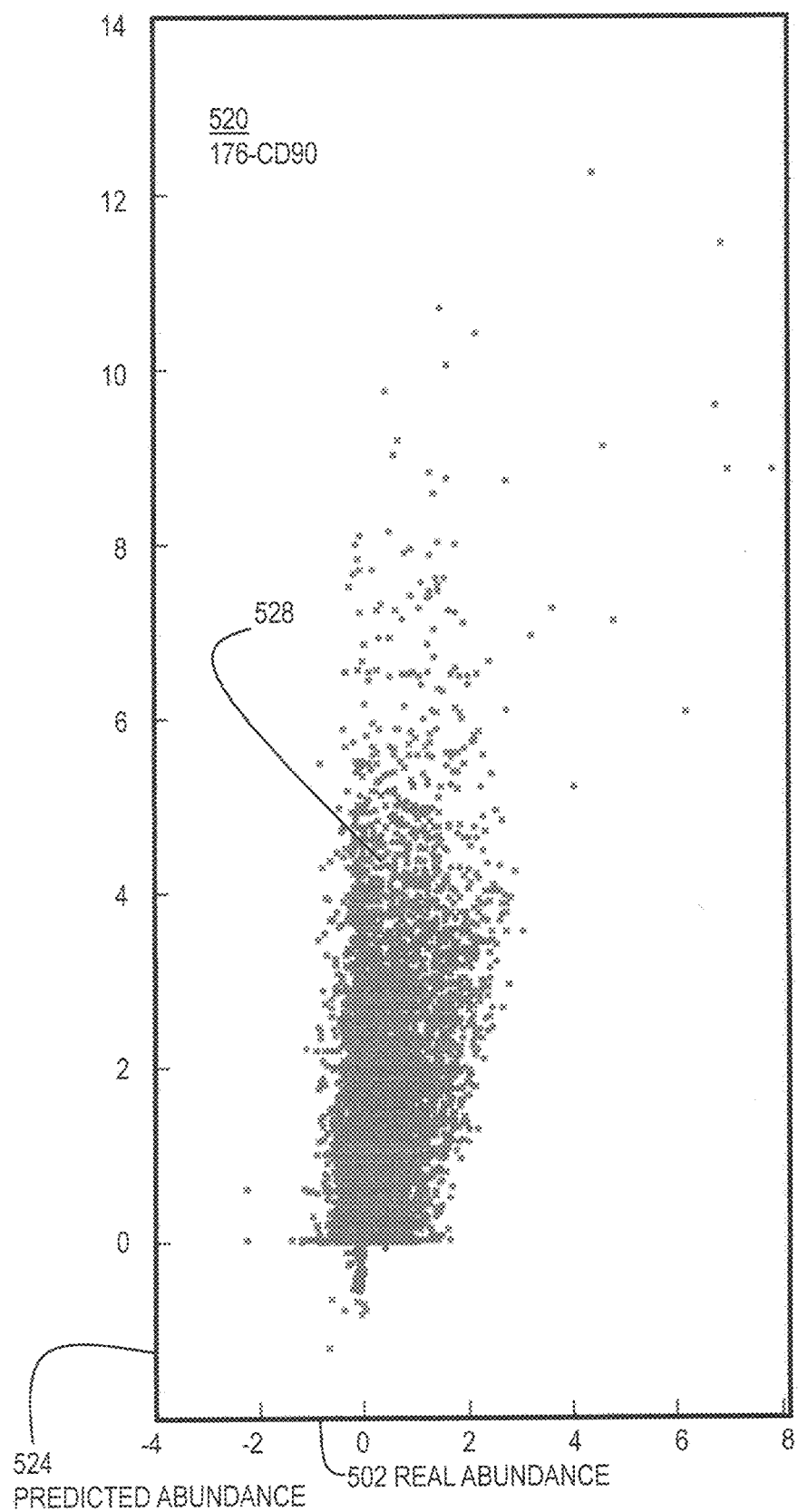

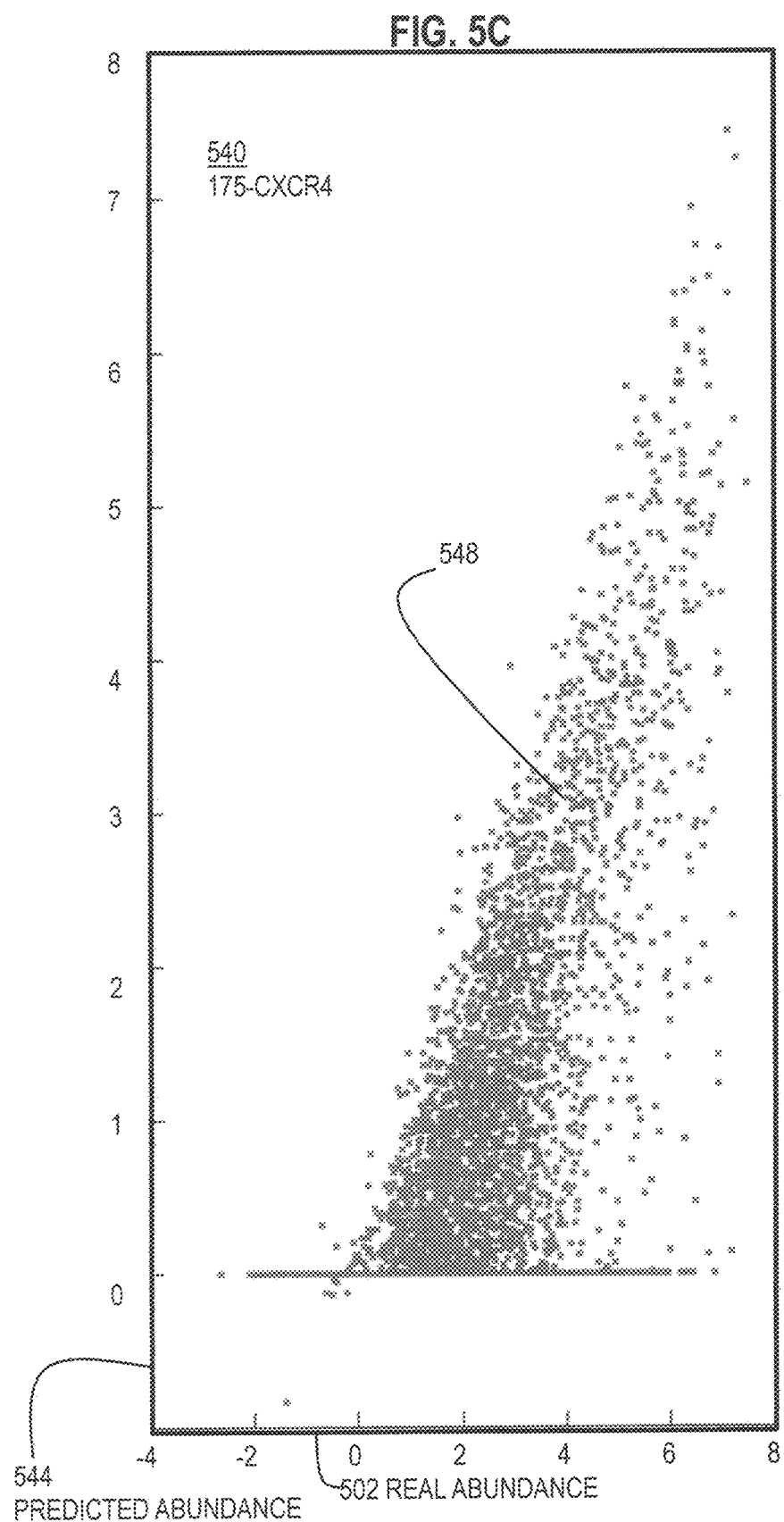

FIG. 10

| | CD19 | CD4 | CD8 | CD61 | CD45RA | CD14 | CD16 | CD3 |
|---|---|---|---|---|---|---|---|---|
| Mass1 | 0 | 1 | 0 | 1 | 0 | 1 | 0 | 0 |
| Mass2 | 0 | 0 | 1 | 1 | 1 | 0 | 1 | 0 |
| Mass3 | 0 | 1 | 1 | 1 | 0 | 0 | 0 | 1 |
| Mass4 | 1 | 1 | 0 | 0 | 1 | 0 | 0 | 1 |

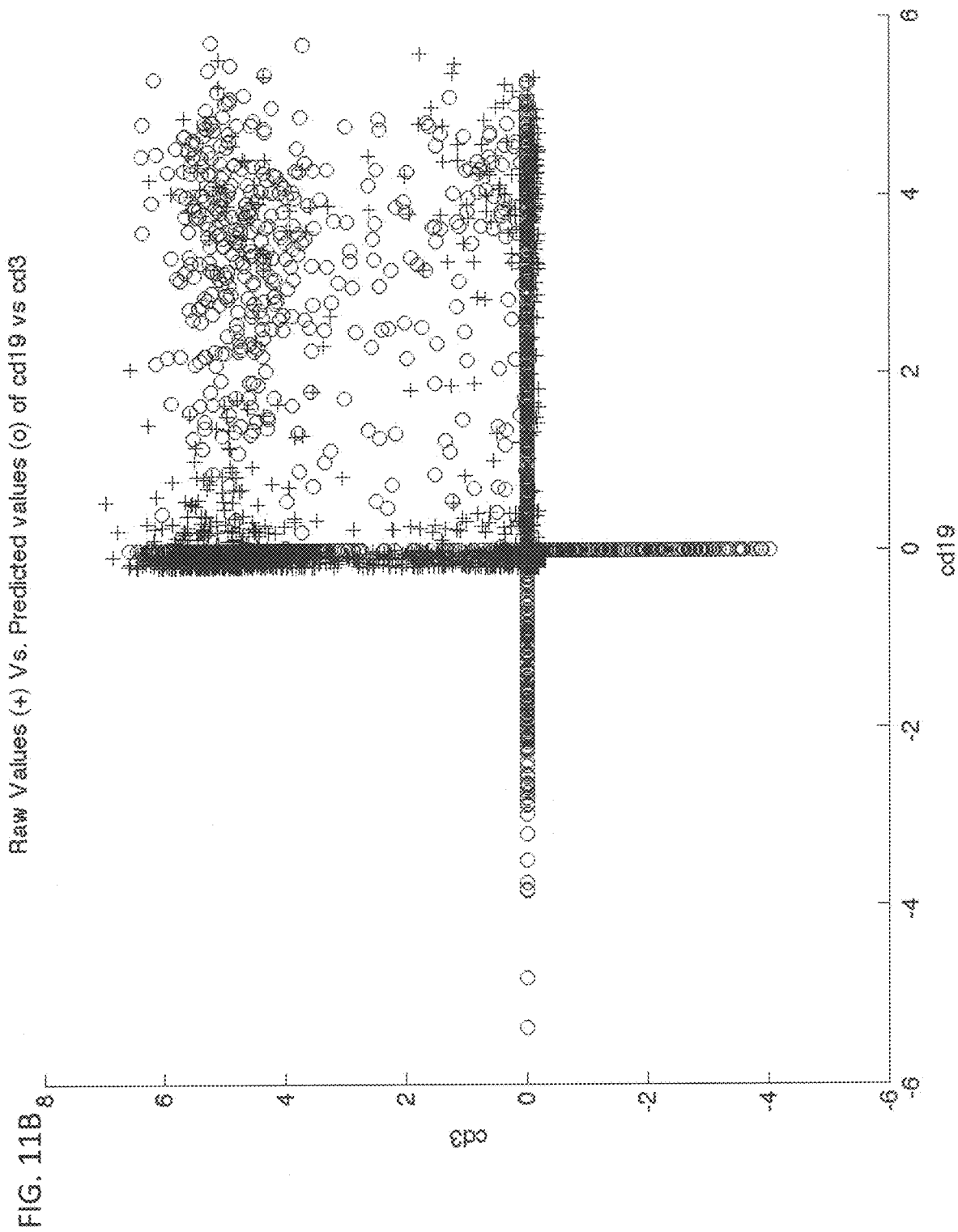

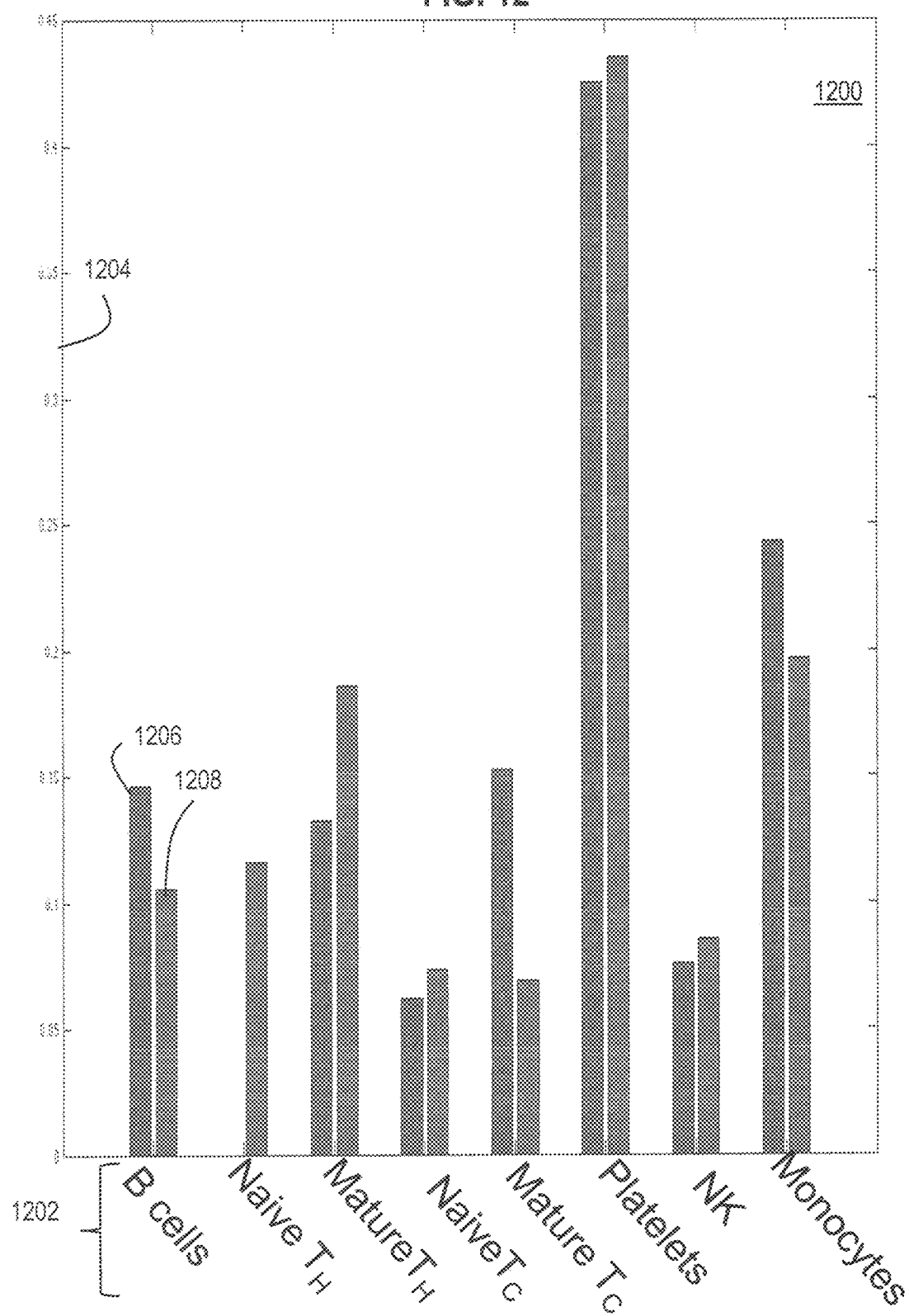

COMPRESSED SENSING FOR SIMULTANEOUS MEASUREMENT OF MULTIPLE DIFFERENT BIOLOGICAL MOLECULE TYPES IN A SAMPLE

CROSS-REFERENCE TO RELATED APPLICATIONS

This application is a continuation of U.S. patent application Ser. No. 13/834,260 filed May 3, 2013 which claims the benefit of Provisional Application No. 61/714,129 filed Oct. 15, 2012, which is incorporated in its entirety.

STATEMENT OF GOVERNMENTAL INTEREST

This invention was made with Government support under contract HV000242 awarded by the National Institutes of Health. The Government has certain rights in this invention.

BACKGROUND OF THE INVENTION

Cytometry is measurement technology enabling quantification of biological cell properties. Flow cytometry enables characterization of protein abundances in and on individual cells by detecting fluorescent labels attached to protein-specific probes, which typically are represented by antibodies. Only about a dozen different proteins can be simultaneously measured easily because of the overlap in the emission spectrum of fluorophores. As the number of measured fluorophores increases, the ability to discern each distinct emission signal diminishes, such that only about a dozen can be profiled in a manner that allows determination of the signal strength of each distinct fluorophore with reasonable levels of signal to noise. This small number has long been a limitation of conventional fluorescence based flow cytometry. Very recently, the number that can be simultaneously measured has leapt to just over 45 through the advent of mass spectrometry based flow cytometry. In this approach, each probe is labeled with an isotope of an element (also called a metal tag) that is not naturally found in biological organisms. The relative abundances of such isotopes are profiled in a Cytometry Time Of Flight ("CyTOF") mass spectrometer. The cell, with its bound labeled probes, is reduced to its constituent elemental ions in an argon plasma; and, the distribution of ion masses for each unit charge is determined by different times of flight in the CyTOF. The relative abundance of each mass label is determined by the current at a detector as a function of time—the more massive ions arriving at the detector later than the less massive ions with the same charge. See, for example, Sean C. Bendall et al., "Single-Cell Mass Cytometry of Differential Immune and Drug Responses Across a Human Hematopoietic Continuum," *Science*, vol. 332, pp 687-696, 6 May 2011, the entire contents of which are hereby incorporated by reference as if fully set forth herein, except for terminology that is inconsistent with the terminology presented here. However, this number of about 45 discrete labels still falls short of the large number of proteins critical to biological processes and desirable for characterizing a cell or its function by such processes.

SUMMARY OF THE INVENTION

Techniques are provided for simultaneously determining more different biological molecule types in a sample then there are discrete simultaneously measurable labels being used, using techniques of compressed sensing.

In a first set of embodiments, a method includes labeling each different biological molecule type in a biological sample with a unique combination of a plurality of labels. Each different biological molecule type is selected from a population of M different biological molecules types. The plurality of labels is selected from a population of L different labels; and, M is greater than L. Measurements are obtained of relative abundances of the L different labels in the sample. Relative abundances of up to M different biological molecule types in the sample are determined based on the measurements and a method of compressed sensing.

In another set of embodiments, a method includes determining a set of L different labels for which abundance can be measured and a set of M different biological molecule types to be detected. The method also includes determining an assignment matrix that indicates a unique combination of different labels for each molecule type, and obtaining measurements of abundances of labels in a biological sample. Abundances for up to M different molecule types in the biological sample are determined based on the measurements and techniques of compressed sensing.

In various other sets of embodiments, an apparatus or computer-readable medium or kit is configured to perform one or more steps of the above methods.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2 is a block diagram that illustrates an example complex assignment matrix that assigns a unique combination of labels to a unique protein, where the number of labels is less than the number of proteins, according to an embodiment;

FIG. 3 is a flow diagram that illustrates, at a high level, an example method for determining the relative abundances of more molecule types in a sample than number of labels, according to an embodiment;

FIG. 4A and FIG. 4B are block diagrams that illustrate example experimental setups for measuring relative abundances of labels associated with molecules in cells, according to various embodiments;

FIG. 5A and FIG. 5B and FIG. 5C are graphs that illustrate example agreement between actual abundances and abundances estimated using fewer labels and compressed sensing for three different proteins, respectively, according to various embodiments;

FIG. 10 illustrates a selected example assignment matrix for validation experiment using four mass labels for eight markers represented by proteins CD19, CD4, CD8, CD61, CD45RA, CD14, CD15 and CD3, according to an embodiment;

FIGS. 11A and 11B are scatter plots that illustrate example agreement of raw and predicted values of markers CD8 vs. CD3 and CD19 vs. CD3 respectively, two at a time, using the assignment matrix of FIG. 10, according to an embodiment;

FIG. 12 is a bar graph that illustrates example agreement in raw and predicted cell type classification, using the assignment matrix of FIG. 10, according to an embodiment;

DETAILED DESCRIPTION

Figure 1A:
FIG. 1A is a block diagram that illustrates an example simple assignment matrix that assigns each unique label to a unique protein, where the number of labels and the number of proteins are equal.

A method and apparatus are described for simultaneously determining multiple different biological molecule types in a sample with greater dimensionality than number of labels. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. In the following, several references are cited. The entire contents of each of these references are hereby incorporated as if fully set forth herein, except for terminology that is inconsistent with the terminology used herein.

Some embodiments of the invention are described below in the context of characterizing a cell of a human immunology system by the detection or quantification of receptor proteins (called receptors) on the cell's outer membrane. However, the invention is not limited to this context. In other embodiments, other biological molecules are detected or quantified by relative abundance, including, for example, nucleic acids, lipids, and other proteins, in similar or different cells in humans or other animals or in plants or in organisms of other kingdoms. As used herein, any measure of any property of any of these cells in any combination is encompassed by the term "cytometry."

1. OVERVIEW

Compressed sensing has revolutionized signal acquisition, by enabling high dimensional signals to be measured with remarkable fidelity using a small number of so-called incoherent sensors. Various embodiments are described, which show that flow cytometry parameters, e.g., relative abundances of proteins measured in a flow experiment, can be determined in an analogous manner, yielding a dramatic increase in the effective dimensionality of flow cytometry data.

In flow cytometry, each label that can be attached to a protein and distinguished in a concurrent measurement is called a channel. To achieve the advantages of compressed sensing, flow experiments are modified in various embodiments so that each channel measures a mixture of multiple proteins, and each protein is measured on several of the available channels, using a configuration in which the number of proteins outnumbers the number of channels. In various embodiments, each channel serves as an incoherent sensor of the proteins measured in that channel, e.g., proteins to which that label is attached. The compressed sensing framework is then used to reconstruct computationally the resulting measurements and report the best estimate (also called an inferred value) of the relative quantity of each protein. Useful accuracy is obtained when the experimental conditions sufficiently satisfy the assumptions of compressed sensing, such as incoherent sensors and sparse solution sets in each experiment.

Embodiments are demonstrated using flow datasets in which the above configuration is imposed in silico, on actual datasets collected using standard, non-compressed flow cytometry data. These embodiments show that this approach yields substantial dimensionality improvements while providing estimates of protein abundances that maintain usefully high accuracy. This approach can be used to measure more cell markers than there are labels available or to make better use of fewer labels to determine important cell differences—an advantage in the mass production of assays or laboratories on a chip. At a high level, the concepts of compressed sensing for cytometry are illustrated in FIG. 1A, FIG. 1B and FIG. 2.

Figure 1B:
FIG. 1B is a block diagram that illustrates an example complex assignment matrix that assigns a unique combination of labels to a unique protein, where the number of labels and the number of proteins are equal.

FIG. 1A is a block diagram that illustrates an example simple assignment matrix that assigns each unique label to a unique protein, where the number of labels and the number of proteins are equal. The diagram includes a number of rows for a corresponding number of proteins that can be quantified in a single experiment. For convenience, the proteins are designated $Protein_1$ through $Protein_{31}$. In this example, the number 31 is selected as the number of different proteins that are currently distinguished in a typical CyTOF experiment. Each column represents a different one of the 31 metal tags that serve as labels that can be distinguished concurrently in a typical CyTOF experiment. These 31 metal tags constitute the 31 channels designated $C_1$ through $C_{31}$. If a label is attached to a protein, a value 1 appears in a cell where the corresponding protein and label intersect; otherwise, a value zero appears at that intersection. The matrix of values in all the intersecting cells of all the proteins and all the labels is called the assignment matrix; and, is indicated by the symbol A. Presently, 31 proteins are each labeled with a different one and only one of the 31 metal tags in the simple diagonal assignment matrix depicted in FIG. 1A.

In cytometry experiments, the labels rarely bind exclusively to a protein of interest. Therefore it is usual for a label to be attached to a probe molecule that is known to bind to a single particular protein among the proteins in the experiment. The probe has the desired selectivity if it binds only to one of the proteins in the experiment, e.g., to one of the 31 proteins. The diagram above each column is meant to represent a label, indicated by an oval, attached to an antibody, indicated by divergent appendages, in which the antibody is selective for a particular protein or other biomolecule of interest either inside or on the outer membrane of a cell. The number in the oval indicates the atomic mass of the metal tag, which is distinguishable in a CyTOF experiment from other labels used in other columns.

The simple diagonal assignment matrix of FIG. 1A is straightforward to use to solve for the relative abundances of the 31 proteins. For example, if an abundance of the label of $C_1$ is measured, but not detected in an experiment, then $Protein_1$ is not found in or on the cell type(s) being analyzed. Similarly, if abundance of the label of $C_2$ is found in or on one cell at half the abundance of the label of $C_2$ on a second cell in an experiment, then the $Protein_2$ is twice as common on the second cell than on the first cell. The individual cell or cell type can be characterized by these relative abundances.

The relative abundance of each protein can be determined because there are 31 independent measurements (of the 31 different metal tag masses) to describe the 31 unknowns (the abundances of the 31 proteins). Due to measurement error, it is common practice to make several measurements of the same type of cells. With multiple experiments, the relative abundances are determined by an average of the multiple values of the abundances for each protein.

In more general circumstances, linear algebra provides a solution for a set of unknowns if there is at least one independent equation for each unknown. Such an approach can be used with a more complex assignment matrix. FIG. 1B is a block diagram that illustrates an example complex assignment matrix that assigns a unique combination of labels to a unique protein, where the number of labels and the number of proteins are equal. In this case, each measured abundance of a label, e.g., the label of channel $C_2$, is given by an equation, e.g., a sum of the occurrence of several proteins, such as receptor $Protein_2$ and receptor $Protein_{31}$ for $C_2$. The amount of $Protein_2$ and $Protein_{31}$ can be determined because there are one or more other measurements that depend on different equations for the combinations of the abundances of these proteins, e.g., receptor $Protein_2$ in the fourth column and receptor $Protein_{31}$ in the third and last columns, for $C_3$ and $C_{31}$, respectively. Linear algebra provides a unique solution so long as the number of independent equations is equal to the number of unknowns. Thus, the abundances of 31 different receptor proteins can be determined as long as there are 31 independent equations relating those abundances to known values of the measured label abundances. Again, measurement errors can be reduced by repeating the experiments multiple times and using some known error minimization approach, such as least squares. However, this approach is not used in practice, since it introduces complexity into the experiment without any benefit.

As pointed out in the background, there are more different proteins in or on cells than there are channels. In some embodiments, a more complex assignment matrix is defined that is not constrained by the number of channels. FIG. 2 is a block diagram that illustrates an example complex assignment matrix that assigns a unique combination of labels to a unique protein, where the number of labels is less than the number of proteins, according to an embodiment. The diagram includes a number of rows for a corresponding number of proteins that are to be quantified in a single experiment, according to some embodiments of the compressed sensing approach. For convenience, the proteins are designated $Protein_1$ through $Protein_{60}$. In this example, the number 60 is selected as more than the number of different proteins that are currently distinguished in a typical CyTOF experiment. Each column represents a different one of the 31 metal tags that serve as channels $C_1$ through $C_{31}$, described above. Estimates of the relative abundances of all 60 proteins are possible using the methods of compressed sensing.

The conditions for accurate estimates from compressed sensing includes a biological molecule abundance signal that is sparse, meaning that for any given cell, some of the target biological molecules are at negligible abundance. This condition is satisfied particularly well for surface markers because their expression is often mutually exclusive (e.g. CD3 positive cells are CD20 negative, and vice versa). Another condition is that the channels should be highly incoherent. An exact definition of incoherence can be found in Candes, E. J., and M. B. Wakin, "An introduction to compressive sampling," *IEEE Signal Proc Mag.*, v 25, no. 2, pp 21-30, 2008; but, intuitively, incoherence relates to the diversity of markers that are measured in each channel. The greater the variety of markers measured in each channel, the larger the incoherence. In other words, the assignment matrix, e.g., portrayed in FIG. 2, should not follow a consistent pattern. For cytometry experiments described herein, it is possible to control the assignment matrix, because an arbitrary assignment matrix can be formed by selecting the labels to be attached to each protein in the set of M proteins. This ability to control the assignment matrix is a great advantage of the applications proposed here. The magnitude of the dimensionality increase, e.g., the extent to which M outnumbers L, depends on the extent to which these two conditions are satisfied. The compressed sensing literature contains many theoretical guarantees about this dimensionality increase. The majority of these results concern assignment matrices with some degree of randomness, such as the guarantees in Candes E & Plan Y "A Probabilistic and RIPless Theory of Compressed Sensing," *IEEE Transactions on Information Theory*, v 57, no. 11, pp 7235-7254, 2010. In the embodiments described herein, the assignment matrix is fixed and can be designed to be suitable for a given purpose. Theoretical guarantees for fixed matrices are discussed in the papers by Candes E. J. and J. Romberg J. "Quantitative robust uncertainty principles and optimally sparse decompositions," *Found Comput Math*, v 6, no. 2, pp 227-254, 2006; and Tropp J. A. "On the conditioning of random subdictionaries," *Applied and Computational Harmonic Analysis*, v 25, no. 1, pp 1-24, 2008. Finally, the notions of sparsity and incoherence are all relative to the basis in which the measurements are made. With an optimal choice of basis, even seemingly non-sparse signals may be measured.

In the compressed sensing framework, if these conditions of sparse signal and incoherent assignment matrix are well satisfied, then $\ell_1$ minimization can be used to compute the abundances of M proteins from L measurement channels with high accuracy, where $\ell_1$ indicates a size of a vector given by the sum of absolute values of vector elements. In an illustrated embodiment, compressed sensing involves finding a solution for the unknown molecular abundances, designated by the vector x, subject to a regularization penalty based on the metric $\ell_1$ given by Equation 1.

$$\ell_1 = \Sigma \text{ of elements of } |A x - o| \quad (1)$$

where o is a vector of the observations (abundances of L labels). Practically, the absolute value of a quantity is computed quickly as a square root of the quantity squared. Also, to ensure a sparse solution, the least significant abundances are rendered negligible by adding a term that multiplies the unknown abundances by a compressed sensing parameter λ, in some embodiments. The resulting practical equation is given in some embodiments by minimizing the difference Δ given by Equation 2.

$$\Delta = \Sigma \text{ of elements of } \{\text{square root of } (A x - o)^2\} + \lambda |x| \quad (2)$$

Lambda (λ) is a parameter (having a positive value) that helps express how sparse the signal is. By adding the term λ |x|, many computed x entries are driven to zero, ensuring a sparse solution. The larger the value of λ, the more sparse the solution is forced to be. It is noted that, if a signal is not naturally sparse enough, it is possible, in some embodiments, to mathematically tweak the treatment of the experimental results to create more negligible abundances—for instance, by computing each protein level relative to a reference protein with near median abundance. In some embodiments, results from several experiments on the same cell type are combined and a set of equations of type 2 with different values for the vector o are obtained and solved by regression methods for best estimates of x considering all measurements o from multiple experiments.

In compressed sensing, regularization by $\ell_1$ is only one approach. In other embodiments, other metrics are used, such as the nuclear norm. There are very many approaches in the literature, including ones that utilize $\ell_1$ but in a different way than described in Equation 2. In various embodiments, these various approaches to compressed sensing are utilized, alone or in some combination.

FIG. 3 is a flow diagram that illustrates, at a high level, an example method 300 for determining the relative abundances of more molecule types in a sample than number of labels, according to an embodiment. Although steps are depicted in FIG. 3 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 301, a set of labels with a number L of members is determined. For example a set of about a dozen (L≈12) fluorophores that fluoresce at different wavelengths that can be measured concurrently in a flow cytometry fluorescence experiment, or a set of over 30 (L≈31) metal tags of different atomic weights that can be measured concurrently in a CyTOF experiment, or both, are determined. Thus, in some embodiments, step 301 includes selecting the plurality of labels from a population of about 20 different fluorophores with corresponding different fluorescent wavelength. Similarly, in some embodiments, step 301 includes selecting the plurality of labels from a population of about 30 different isotopes of elements which are not otherwise found in biological organisms and which have ions of different corresponding masses. In some simulated embodiments described below, the number L of labels is chosen to be between 12 and 30.

In step 303, a set of biological molecule types, with a number M of members, is determined in which the molecule types are to be detected or quantified by relative or absolute abundance in a biological sample. The set is determined so that M is greater than L. For example, a set of 60 receptors that are found on various cells of the human immune system are defined so that individual cells can be characterized by the abundances of these receptors. In some simulated embodiments described below, in which the number L of labels is chosen to be between 12 and 30, the number M of proteins is taken to be 31 (the number that can be determined in a CyTOF experiment used as a gold standard for testing the method). In some embodiments, the biological sample comprises whole cells and each different protein is a different receptor for an outer cell membrane of at least some cells. In some embodiments, the biological sample comprises permeabilized cells and each different protein is found inside at least some cells. In some embodiments, the sample and target molecules are selected so that each cell includes a number N of the biological molecule types, wherein N is less than about half of M to promote sparse solutions sets well suited for compressed sensing methods.

In step 305, an assignment matrix is determined for a set of one or more experiments. The assignment matrix is determined so that unique labeling is provided for each molecule type with a unique combination of the L labels. Thus the assignment matrix is M×L (M rows by L columns). For example, values of 0 or 1 or other (including fractional values in some embodiments) are determined for each element of a matrix with 60 rows and 31 columns. In some embodiments, the values are assigned at random.

In some embodiments, step 305 includes testing whether any row is a linear combination of any other one or more rows. If so, the row is assigned another set of values (e.g., at random) and tested again. This process is repeated until the assignment matrix is known to be well conditioned.

In some embodiments, step 305 includes retrieving a previously stored assignment matrix determined to be effective in similar contexts, such as in a test case with known abundances of the molecules, as described later with reference to step 315. Thus, in some embodiments, determining the assignment matrix that indicates the unique combination of different labels for each molecule type further comprises determining the assignment matrix that provides acceptable performance for a test set with known abundances of the different biological molecule types.

In step 307, a value for the compressed sampling parameter λ is determined. In some embodiments, step 307 includes retrieving a previously stored value for X determined to be effective in similar contexts, such as in a test case with known abundances of the molecules, as described later with reference to step 315. Thus, in some embodiments, determining the value for the parameter X comprises determining the value for the parameter λ to provide acceptable performance for a test set with known abundances of the different biological molecule types. In some embodiments, the value of λ is set to be small, e.g., about 0.001.

In step 309, each of the M target molecule types in or on a cell of a sample are labeled according to the assignment matrix. In an example experiment, this means that each protein-specific antibody is made in several variations; in each, it is tagged with one of the labels to which it has been assigned. During the staining step of the flow cytometry experiment, antibodies with the various tags are pooled, such that each protein is effectively measured on all the channels to which it has been assigned somewhere on the individual cell. For example, using the assignment matrix of FIG. 2, multiple copies of a probe molecule type known to bind to Protein$_{60}$ are each labeled with one of the labels of $C_2$ or $C_3$ or $C_{31}$ in equal proportions as indicated by the assignment matrix. In some embodiments, each copy of the probe molecule type is labeled with more than one of these labels, as described in more detail in a later section. In some embodiments, step 309 includes removing labels that have not attached to a probe, e.g., by rinsing with a first buffer solution, or removing probes that have not attached to a label, e.g., by rinsing with the same or different buffer solution, or both. In some embodiments, rinsing is part of the standard protocol for making the conjugated antibodies.

The labeled probe molecules are then contacted to target biological molecules from cells in a biological sample. In some embodiments, the cells in the sample are whole cells and only molecules on the surface of the cell are available for contacting the labeled probes. Thus, the biological sample comprises whole cells and each different protein is a different receptor for an outer cell membrane of at least some cells. In some embodiments, the cells in the sample are fixed and permeabilized cells, and molecules on the surface and interior of the cell are available for contacting the labeled probes. Thus, the biological sample comprises permeabilized cells and each different protein is found inside at least some cells. As a result of this contact, molecules of the target biological molecule types bind to the labeled probes. In some embodiments, step 309 includes removing probes that have not bound to a target molecule type, e.g., by rinsing with a buffer solution.

In some embodiments, the target molecules are proteins, including receptors. In such embodiments, step 309 includes attaching each label in the unique combination to an antibody that binds to the different protein to produce a plurality of labeled antibodies, and contacting the biological sample with the plurality of labeled antibodies for each different protein. Therefore, in some embodiments, each different biological molecule type is a different protein; and step 309 includes attaching each label in the unique combination to an antibody that binds to the different protein to produce a plurality of labeled antibodies. In some of these embodiments, step 309 also includes contacting the biological sample with the plurality of labeled antibodies for each different protein.

In step 311, measurements of abundances of labels in the biological sample are obtained. In some embodiments, step 311 includes performing the measurements, e.g., with a flow cytometry apparatus as depicted in FIG. 4A or a CyTOF apparatus as depicted in FIG. 4B. The measurements yield, for each channel, the summed signal from all of the proteins assigned to that channel. In some embodiments, step 311 comprises receiving measurements previously stored or published, e.g., entered manually or retrieved from a local computer-readable medium or downloaded from a remote device connected by a network, such as a local area network or public Internet, as described in more detail below with reference to FIG. 8 and FIG. 9. Thus step 311 includes obtaining measurements of relative abundances of the L different labels in the sample. In some embodiments using fluorescent labels, step 311 involves obtaining measurements of intensity of each of the corresponding fluorescent wavelengths. In some embodiments using non-biological elements as tags, step 311 involves reducing the sample to ions of its constituent elements and obtaining measurements of abundance of each of the corresponding masses in a time of flight mass spectrometer.

In step 313, abundances of up to M target molecule types in the biological sample are determined based on the measurements and a method of compressed sensing. This determination is made by finding, for each cell, the best values of protein abundances x that minimizes Equation 2. By constraining the solution and the magnitude of the reconstructed abundances using the $\ell 1$ penalty and the parameter $\lambda$, this solution tends to force as many of those protein abundances as possible to be zero. For example, using a computer system of FIG. 8 or chip set of FIG. 9, described below, Equation 2 is minimized using any process known in the art, such as described in more detail in the next section. Thus, step 313 includes determining relative abundance of up to M different biological molecule types in the sample based on the measurements and a method of compressed sensing. In some embodiments, the method of compressed sensing comprises selecting abundances for up to M different molecular types by minimizing an order one distance metric designated $\ell_1$ between computed and measured abundances of the L different labels. In some embodiments, the method of compressed sensing comprises selecting abundances for up to M different molecular types by minimizing a sum of a first term and an order one distance metric designated $\ell_1$ between computed and measured abundances of the L different labels, wherein the first term is a parameter $\lambda$ times a computed abundance of the biological molecule.

In step 315, the results of the computation are compared to actual abundance values, if known. In some of these embodiments, step 315 includes determining updated values for the assignment matrix A or $\lambda$, or both, to achieve better agreement with the known abundances. Thus, a value for the parameter $\lambda$ is chosen to provide acceptable performance for a test set with known abundances of the different biological molecule types. In embodiments in which assignment matrix A is updated, the unique combination of labels for each different molecule type is chosen to provide acceptable performance for a test set with known abundances of the different biological molecule types. In some embodiments without known abundances of the target molecules in the sample, step 315 is omitted.

Thus, in some embodiments, the method is run in 'continual improvement' mode by assessing the correctness of each run and formulating improved assignment matrices and/or additional constraints for the optimization step. Assessing correctness can be done using the validation procedures described below. When validation procedures are not in place, a more passive validation can be performed by inspecting the predicted data for patterns derived from gold standard datasets. This can include biological prior knowledge regarding correlative relationships (as described below, these can include knowledge of mutually exclusive markers) or patterns extracted from a relevant gold standard dataset.

In step 317, it is determined whether there is another sample to analyze. If not, the method ends. If there is another sample, then control passes back to step 309 to apply labels to next biological sample.

In some embodiments, method 300 is repeated for a different set of proteins and labeled probes using unique combinations not in the prior A matrix, and an extended A matrix is developed by block diagonals, as described in more detail below.

Using the method 300, very valuable applications are enabled. For the multitude of facilities for which a CyTOF is not available, the number of measurable entities can be expanded accordingly. Abundances for many more than 31 proteins can be determined with a concurrent CyTOF measurement. The extended number of protein abundances can be used to characterize human T cells; and, a person's immunity can be assessed by the distribution of different T cell types found in a blood sample. The extended number of protein abundances can be used to characterize single cells in a plethora of contexts. One popular application is the characterization of the immune system with respect to the fraction of different types of immune cells found in a blood sample, another is characterization with respect to the functionality and functional response of cells in a sample, via profiling of the internal cell proteins. In some embodiments, the method enables subsampling that can be moved to a smaller or cheaper device that is competent to do cell classification accurately with fewer labels than is used without compressed sensing.

Furthermore, the process can be generalized for any application in which biomolecules are profiled via a limited set of detectors, including scenarios outside the scope of cytometry, for instance, any application employing a limited set of labels. One example is a microfluidics based mRNA characterization platform, in which each well location in a 96-well plate serves as a detector. In this context each well location can be used to measure a combination of mRNA molecules in a similar format to the one described above for cytometry.

2. SOLUTIONS TO EQUATIONS

Once it is demonstrated that the cytometry biological molecule abundance determination problem can be cast as a regression problem, the methods of compressed sensing can be considered to be applied to solve the regression problem.

Compressed sensing is a theoretical and applied framework that enables the recovery of a signal with high accuracy from relatively few measurements. In the context of the example regression formulation, the signal is the set of values of the M target biological molecule abundances given by vector x, the sensors are the L channels (e.g., labels that can be distinguished in one concurrent experiment, such as 12 fluorophores with distinct fluorescent wavelengths, or 31 metal tags with distinct masses, attached to antibodies with selectivity for the target biological molecules), and the measurements are the label abundances (e.g., intensity of the fluorescent or mass measurement in each channel). Compressed sensing enables the use of relatively few measurements (in L channels) to infer the abundances of the M target biological molecules (M>L).

The application of compressed sensing to regression is achieved by imposing an $\ell_1$ regularization penalty on the regression problem (e.g., see Tibshirani R "Regression shrinkage and selection via the Lasso," *J Roy Stat Soc B Met* v 58 no. 1, pp 267-288, 1996). Several compressed sensing approaches have been developed to accomplish this task. In an illustrated embodiment, Equation 2 is used. In some embodiments, the lasso penalty for linear regression is utilized with its generalization for logistic regression (e.g., see Friedman J, Hastie T, & Tibshirani R "Regularization Paths for Generalized Linear Models via Coordinate Descent," *J Stat Softw* v 33 no. 1, pp 1-22, 2010). In other embodiments, other approaches are utilized, such as the Dantzig selector (e.g., see Candes E & Tao T "The Dantzig selector: Statistical estimation when p is much larger than n," *Ann Stat* v 35 no. 6, pp 2313-2351, 2007) for linear regression and suitable generalizations for logistic regression (e.g., see James G M & Radchenko P "A generalized Dantzig selector with shrinkage tuning," *Biometrika* v 96 no. 2, pp 323-337, 2009). Other generalizations that capture related notions of sparsity, for example, the nuclear norm penalty (e.g., see E. J. Candès and B. Recht, "Exact matrix completion via convex optimization," *Found. of Comput. Math.*, v 9, pp 717-772, 2008) for low-rank matrices is used in some embodiments. Any penalty known in the art may be used.

For example, using the lasso penalty embodiment, one would solve the optimization problem given by Equation 3.

$$\min_x \|A x - o\|_2^2 + \lambda \|x\| \quad (3)$$

Accurate inference of abundances is ultimately dependent on two important characteristics of the particular application. These two characteristics are the sparsity of the molecule abundances to be inferred, and the coherence of the label abundance measurements used for inference. The compressed sensing literature contains many theoretical guarantees about the expected number of measurements required, denoted by m, given a signal of length n with s non-zero entries and a sensor matrix X (the assignment matrix A) with coherence μ in regression. The majority of these results concern sensor matrices with some degree of randomness (e.g., see Candes E & Plan Y "A Probabilistic and RIPless Theory of Compressed Sensing," *IEEE Transactions on Information Theory*, v 57, no. 11, pp 7235-7254, 2010). In the illustrated embodiment, the assignment matrix can be varied by changing the mixture of labels attached to various probes, such as antibodies for receptors. Theoretical guarantees for fixed matrices are discussed (e.g., see Candes E J & Romberg J "Quantitative robust uncertainty principles and optimally sparse decompositions," *Found Comput Math* v 6, no. 2, pp 227-254, 2006; and Tropp J A, "On the conditioning of random subdictionaries," *Appl Comput Harmon A* v 25 no. 1, pp 1-24, 2008).

In general, most results relate m to an increasing function of n, s, and μ. In the context of the illustrated embodiment, n is the total number M of target molecules, s is the number of molecule abundance values that are non-negligible, and μ is the coherence of the assignment matrix A. Thus, if only a small number of the molecule abundances on a particular cell type are non-negligible (i.e., s is small), then only a small number of channel measurements are needed for accurate inference of the metric value. The role that μ plays is slightly more subtle (the formal definition of μ can be found in Candes E J & Wakin M B "An introduction to compressive sampling," *IEEE Signal Proc Mag* v 25, no. 2, pp 21-30, 2008). Intuitively, coherence relates to the diversity of molecular abundances that contribute to the intensity of each channel. The greater the variety of molecular abundances participating in each experimentally characterized channel intensity, the smaller the coherence. Thus, to minimize the number of experimental measurements needed, one needs to minimize the coherence of the assignment matrix. This implies that the channel types must incorporate as wide a range of molecular abundances types as possible. However, the degree to which the coherence of channel types can be controlled is dependent on the application. For the cytometry applications, the choice of labels comprising the set of channel types directly impacts the coherence of the assignment matrix.

In some embodiments, the regression equations of Equation 2 for multiple measurement vectors o are solved using methods of compressed sensing. All regressions are regularized using the lasso penalty.

A compressed sensing parameter, known as the regularization parameter), adjusts the expected degree of sparsity of the measured biomolecules with non-negligible values. Values for these parameters are determined by fitting procedure using a training dataset where the values of the target molecule abundance, the values of the label intensities and the assignment matrix are known, e.g., during step 315 described above.

An $\ell_1$-regularized multinomial logistic regression is performed using commercially or freely available software, such as the R-based glmnet package (e.g., see Friedman J, Hastie T, & Tibshirani R "Regularization Paths for Generalized Linear Models via Coordinate Descent," *J Stat Softw*, v 33, no. 1, pp 1-22, 2010) available online at subfolder i01 of folder v 33 at World Wide Web (WWW) domain jstatsoft in domain category org.

3. EXPERIMENTAL SETUPS

FIG. 4A and FIG. 4B are block diagrams that illustrate example experimental setups for measuring relative abundances of labels associated with molecules in cells, according to various embodiments. Cytometer experimental setups are performed according to methods and equipment that are well known in the art (e.g., see Krutzik and Nolan, "Intracellular phospho-protein staining techniques for flow cytometry: monitoring single cell signaling events" *Cytometry*, v 55 (no. 2), pp 61-70, 2003, the entire contents of which are hereby incorporated by reference as if fully set forth herein). FIG. 4A and FIG. 4B are presented to diagram conceptually the various processes that are performed in various vessels, called chambers herein. These experimental setups are used to perform or provide data for steps 309 and 311 of method 300, in some embodiments. Although processes, equipment, and data structures are depicted in FIG. 4A and FIG. 4B as integral blocks in a particular arrangement for purposes of illustration, in other embodiments one or more equipment or processes or data structures, or portions thereof, are arranged in a different manner, or combined on the same or different equipment or processes or data structures, or are omitted, or changed in some combination of ways. Any flow cytometer may be adapted for use in various embodiments, such as available from the BD BIOSCIENCES™ of Franklin Lakes, N.J. CyTOF equipment is available from DVS SCIENCES INC.™ of Toronto, Canada.

FIG. 4A is a block diagram that illustrates an example flow cytometry setup 400 using fluorescent labels. The setup 400 includes a sample input chamber 410 in flow communication with a pump 402, cell permeabilizing chamber 404, label input chamber 420, probe binding chamber 406 and scanning portion 408. The sample input chamber 410 is configured to introduce a sample to be analyzed, often mixed with a fluid buffer, into the equipment. A sample 419 includes one or more sample cells of one or more cell types to be characterized by one or more biological molecules found in or on the cell, and is placed in the sample input chamber 410. A pump 402 is configured to cause the fluid with sample cells to move through the equipment, ultimately as fluid flow 409. In some embodiments, the setup includes the cell permeabilizing chamber 404, such as a separate test tube or multiwell plate configured to rupture an outer membrane of one or more cells of the sample cells in order to release one or more biological molecule types from inside the one or more sample cells of the sample 419. In some embodiments, only biological molecules on the surface of the sample cell are of interest and the cell permeabilizing chamber 404 is bypassed or omitted. Although sample 419 with cells is depicted for purposes of illustration, the sample 419 itself is not part of the experimental setup 400.

The label input chamber 420 is configured to introduce fluorophore labeled probes 429, often in a buffer solution, into the equipment. The probes are formed as described above with reference to step 309 of method 300—either in chamber 420 or are formed externally, e.g., in a separate test tube or multiwell plate, and introduced via chamber 420. Although fluorophore labeled probes 429 are depicted for purposes of illustration, in some embodiments, they are not part of the experimental setup 400. However, in some embodiments, kits for forming the fluorophore labeled probes are part of the experimental setup, as described in more detail below.

Probe binding chamber 406 is configured to contact the labeled probes with the target molecules from the sample 419, as described above with reference to step 309 of method 300. In some embodiments, excess labeled probes are removed in probe binding chamber 406 or are contacted externally, e.g., in a separate test tube or multiwell plate, and introduced via chamber 406.

Scanning portion 408 of equipment is configured for allowing an excitation beam 431 to illuminate the fluid flow 409 encompassing labeled probes bound to target molecules and is further configured to allow fluorescent emissions 433 to exit the equipment. For example, the scanning portion 408 includes one or more optical windows. A light source 430, such as a laser, illuminates the fluid flow 409 with the excitation beam 431 at one or more electromagnetic wavelengths that occur in or near an optical wavelength band of visible light. A optical detector, such as a charge coupled device (CCD) array, detects fluorescent emissions at up to a number L (e.g., about 12) different electromagnetic wavelengths that occur in or near an optical wavelength band of visible light but differ from the wavelength of excitation beam 431.

Figure 8:
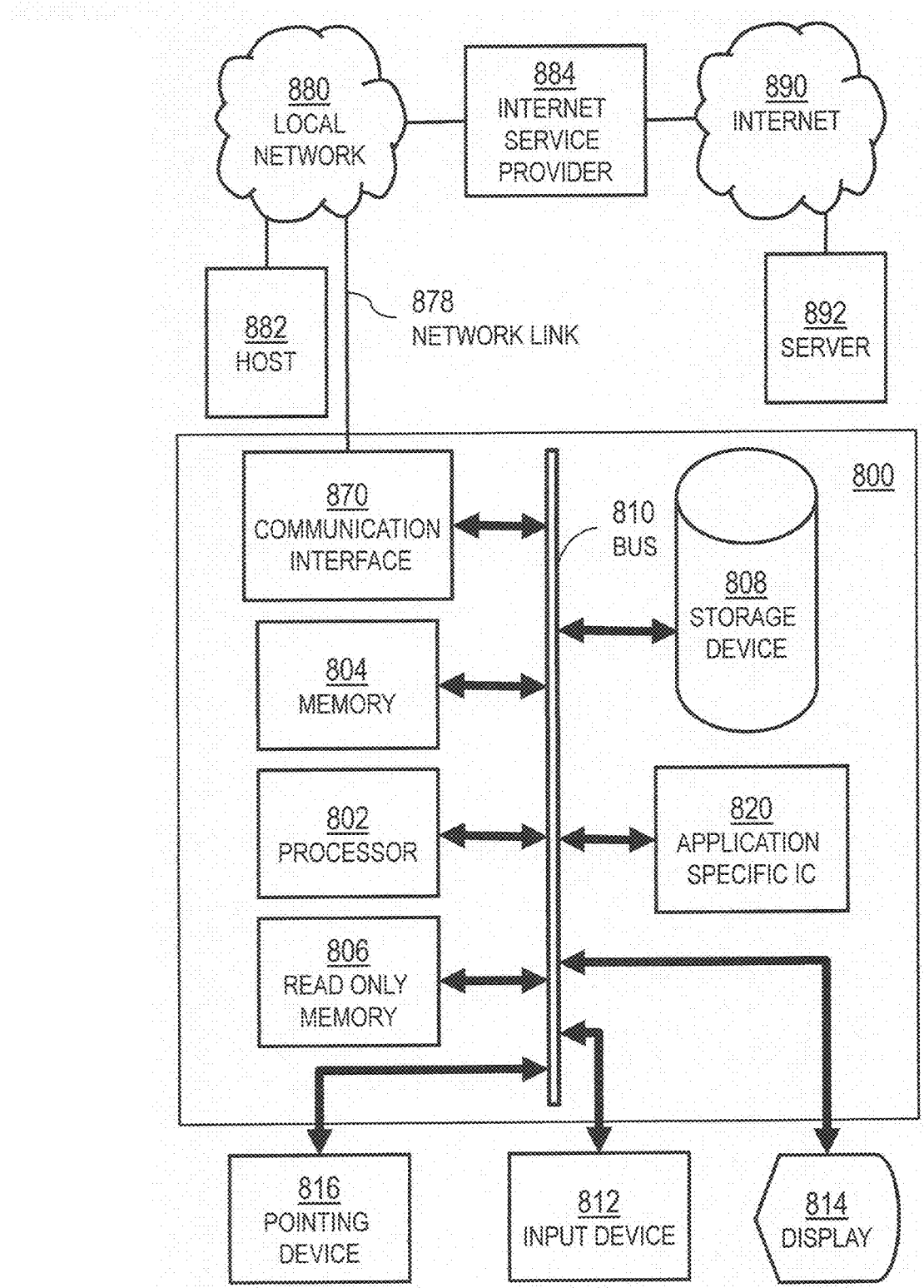
FIG. 8 is a block diagram that illustrates a computer system upon which an embodiment of the invention may be implemented.
Figure 9:
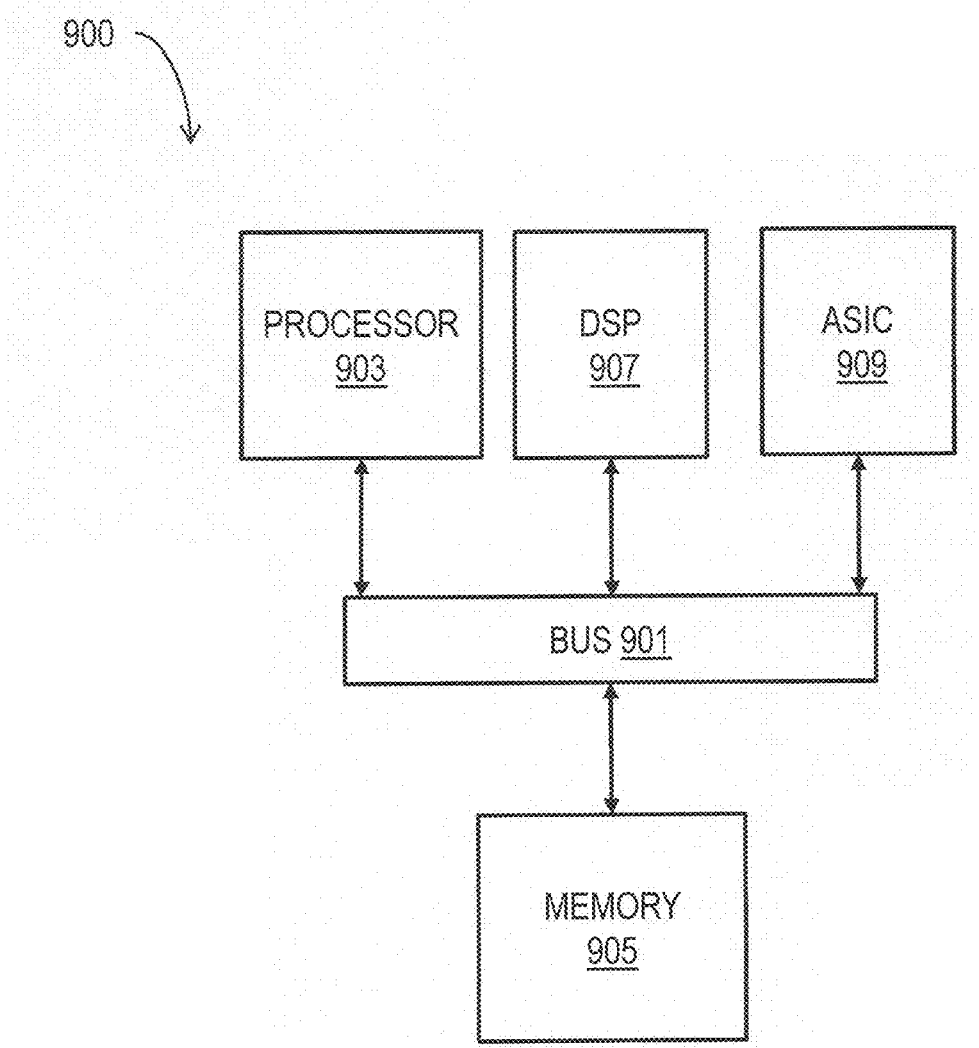
FIG. 9 illustrates a chip set upon which an embodiment of the invention may be implemented.

A controller/processor system 440 is configured to control one or more of the pump 402, the light source 430 or the optical detector 434, and collects and processes and stores data based on the signals received at the optical detector 434. The controller/processor system 440 is implemented on one or more computer systems, as depicted in FIG. 8, including one or more application specific integrated circuits (ASICs), or on one or more chip sets, as depicted in FIG. 9, or some combination. The controller/processor system 440 is configured to determine the absolute or relative abundance of the labels in the fluid flow 409, e.g., by determining the intensity at each of up to a number L (e.g., about 12) different wavelengths detected at optical detector 434. Thus, in some embodiments, step 311 of method 300 to obtain the observation vector o is performed using the light the scanning portion 408, the light source 430, the optical detector 434 and the controller processor system 440.

The controller/processor system 440 includes a compressed sensing cytometry module 442 that is configured to perform step 313 of method 300, which is to determine the vector x of the relative abundances of up to M target biological molecules in one or more biological samples 419 based the measurements o and a method of compressed sensing. For example, the module 442 performs step 301 to determine the characteristics of the L labels, step 303 to determine the M target biological molecules, step 305 to determine the assignment matrix A and step 307 to determine the parameter $\lambda$. In this example embodiment, the module 442 is further configured to retrieve stored values of the assignment matrix A and the value of parameter $\lambda$ and use those values to compute values for the vector x that minimizes the value of $\Delta$ in Equation 2. In some embodiments, the module 442 also retrieves stored data that indicates actual abundances of one or more target molecules and uses that information to update the assignment matrix A or λ or both, as in step 315.

The strategy for deconvolution of the signal into the individual markers can be codified into a software package to be applied to raw data. This package takes as input an assignment matrix and sparsity parameter, λ, as well as the measurements on each channel, and outputs the deconvoluted predicted values for each molecule type (also called a marker herein). It may also be advantageous to input a limited number of controls, for instance, the measurements resulting from each marker being measured independently (this allows resolution of the assignment matrix parameters, e.g., in correspondence with the relative strength of signals in different mass channels). In addition to the basic compressed sensing approach which calls for an $\ell_1$ regularization of the optimization problem, additional constraints can be employed to further improve accuracy. For instance, in some embodiments, a constraint indicating that two or more markers must be treated as mutually exclusive (e.g. CD3 and CD20) can be incorporated. Methods exist for formulating these into a convex optimization problem which can be incorporated into the software. In some embodiments, this software executes in real time using appropriate dedicated hardware, such that the researcher receives the predicted values with no significant delay compared to the time to run an experiment.

In some flow cytometry analysis, gates are drawn around the cells with similar properties. A cell within the gate is sorted. In some embodiments, the controller processor system 440 also controls a cell sorter. In some of these embodiments, real time deconvolution by module 442 determines whether a cell belongs "inside" or "outside" the gate; and, therefore whether the cell is suitable or not for sorting by system 440.

FIG. 4B is a block diagram that illustrates an example CyTOF setup 450 using metal tags as labels. The setup 450 includes a sample input chamber 410 in flow communication with a pump 402, cell denaturing chamber 404, label input chamber 420, probe binding chamber 406, nozzle 452 and time of flight mass spectrometer (TOFMS) 460 configured to introduce a fluid flow 459 into the TOFMS 460. The sample input chamber 410, pump 402, cell denaturing chamber 404, sample 419 with cells and compressed sensing cytometry module 442 are as described above for FIG. 4A. Although sample 419 with cells is depicted for purposes of illustration, the sample itself is not part of the experimental setup 450.

The label input chamber 425 is configured to introduce one or more non-biological element (such as a metal tag) labeled probes 455, often in a buffer solution, into the equipment. The probes are formed as described above with reference to step 309 of method 300—either in chamber 425 or are formed externally and introduced via chamber 425. Although non-biological element labeled probes 455 are depicted for purposes of illustration, in some embodiments, they are not part of the experimental setup 450. However, in some embodiments, kits for forming the fluorophore labeled probes are part of the experimental setup, as described in more detail below.

Probe binding chamber 456 is configured to contact the labeled probes with the target molecules from the sample 419, as described above with reference to step 309 of method 300. In some embodiments, excess labeled probes are removed in probe binding chamber 456.

Nozzle 452 is configured to nebulize droplets of the fluid flow 459 with a single cell or material from a single denatured cell into a vacuum chamber of the TOFMS 460. The vacuum chamber of the TOFMS 460 includes a plasma chamber 462, an electric field accelerator 464, a constant velocity flight path section 466 and a detector 468. The TOFMS also includes a TOFMS controller/processor 469.

The plasma chamber 462 is configured to reduce the cell sample to constituent atoms by intense heat and vacuum. These conditions also induce a deficit of outer shell electrons in metallic elements so that they are positively charged, producing an electrically charged gas (the plasma). The electric field accelerator 464 is configured to cause the charged elements of the same charge to accelerate to the same kinetic energy (given by mass times velocity squared). As a result, the more massive elements have lower velocities than less massive elements of the same charge. The constant velocity flight path section allows the faster, lower mass elements to separate from the slower more massive elements and hit the detector 468 earlier. The time history of current at the detectors gives the relative abundances of the different elements, including the different abundances of the non-biological element labels. The TOFMS controller processor 469 controls the vacuum, the heating in the plasma chamber, the acceleration in the electric field accelerator 464 and the operation of the detector. The TOFMS controller/processor also outputs the current profile with time and converts it to relative abundances of one or more elements, including the abundances of one or more of the labels, such as the metal tags.

A controller/processor system 445 is configured to control one or more of the pump 402 or the TOFMS controller/processor 469, and collects and processes and stores data based on the output from the TOFMS controller/processor 469. The controller/processor system 445 is implemented on one or more computer systems, as depicted in FIG. 8, including one or ASICs, or on one or more chip sets, as depicted in FIG. 9, or some combination. The controller/processor system 445 is configured to determine the absolute or relative abundance at each of up to a number L (e.g., about 31) different elemental masses detected by the TOFMS 460. Thus, in some embodiments, step 311 of method 300 to obtain the observation vector o is performed using the TOFMS 460 and the controller processor system 445.

The controller/processor system 445 includes a compressed sensing cytometry module 442 that carries out one or more steps of the method 300, as described above for FIG. 4A. In some embodiments the compressed cytometry module 442 executes on the TOFMS controller/processor 469. In some embodiments, the system 445 performs one or more of the other functions described above for system 440.

Kits.

The increase in the number of measurable parameters comes at a price; the experimental implementation can require more work, since some markers are advantageously measured on more than one channel, involving more conjugation reactions (or purchase of multiple commercially conjugated markers, each on a different mass channel). This can become cumbersome as the number of assignment matrices that is used in a laboratory setting may be large. In some embodiments, kits are provided for flexible preparation of reagents used to implement one or more assignment matrices. For instance, in some embodiments, antibodies are conjugated to a generic linker region, which is irreversibly attached to a mass-bound polymer via a short incubation. An example procedure for doing so is described in U.S. patent application Ser. No. 12/617,438, published as U.S. Patent Application Publication No. 2010/0151472, the entire contents of which are hereby incorporated by reference as if fully set forth herein.

Thus, in some embodiments, a kit comprises one or more reagents for labeling each different biological molecule type with a unique combination of a plurality of labels. In the kit, each different biological molecule type is selected from a population of M different biological molecules types; the plurality of labels is selected from a population of L different labels that are distinguishable in a measurement apparatus; and, M is greater than L.

Validating Assignment Matrix.

In step 305, as described above, an assignment matrix is determined, e.g., at random or retrieved from a source based on one or more matrices used or found to be effective or acceptable in previous experiments, or some combination, e.g., a random perturbation of a previously used matrix. In step 315 the used assignment matrix is validated or updated based on experimental results. In some embodiments, the selected assignment matrix is validated by non-experimental means in step 305.

In some embodiments, the success of the prediction task relies heavily on the choice of an appropriate assignment matrix (see, e.g. FIG. 7A, described below). A high-performing assignment matrix can be found by assessing the performance of several up to thousands of randomly formulated assignment matrices, as described below with reference to example embodiments, or by discerning principles that would allow the rational design of high performance matrices. For all the methods discussed below, it is advantageous to have a means of assessing the performance of each matrix under consideration.

In some embodiments, a method is used to assess the performance of a proposed matrix, e.g., in step 305. Additionally in some embodiments, or alternatively in other embodiments, after an assignment matrix is selected, a method is used to assess how well the selected assignment matrix performed on a new dataset, e.g., during step 315. Methods for assessing for these purposes are described next.

Assessing Matrices for Selection of Appropriate Matrix.

In the example embodiments described below, a dataset measured using conventional means was used to simulate the dataset that would have been obtained using fewer labels and compressed sensing (for various formulations of the assignment matrix and other parameters), and to assess the reconstructed data with respect to its ability to yield correct classification of cells, using a decision tree classifier trained on the raw (unpredicted) data. Starting with a traditionally measured 'gold standard' dataset and using some system of assessment to assess the predictive ability of the assignment matrix is convenient since the real values are known in such an arrangement.

In cases where the total number of markers to be measured using compressed sensing exceeds the measurement capability of any available technology, it is not possible to obtain a gold standard dataset. For instance, it is possible to measure 60 markers using compressed sensing and a mass cytometer, but it is not currently possible to measure 60 markers in the absence of compressed sensing, so for prediction of 60 markers, no gold standard dataset can be obtained. In this case, a different approach for assessing is formulated based on rational design. For example, if a rational design principle is based on using measurements of marker subsets, this is used to design the assignment matrix in some embodiments. In some embodiments without such a principle, the selected matrix is decomposed into measurable pieces (e.g., 2 sets of 30 markers each), the approach above is used to make a partial matrix for each, and the multiple partials for the pieces are combined into one matrix. This matrix may be less optimal than one designed on the whole dataset, but its performance is still optimized to a degree, and is quantifiable using the same approaches as described above Assessing Performance of a Previously Selected Matrix on a New Dataset.

Once a matrix has been selected and an experiment performed, it is useful to assess how well the prediction performed in the new dataset. This may be done by splitting a sample and running two side by side experiments, one using compressed sensing and one using the standard flow approach. Subsequently, the compressed dataset can be compared to the gold standard dataset, with respect to all available parameters: percent of different cell types observed, level of various markers, phenotypic characteristics of cells observed and so on. If the number of parameters measured is too large to measure simultaneously using standard approaches, it is straightforward to measure the gold standard using 2 or more sets of measurements. This affects the ability to assess the compressed dataset against the gold standard very minimally (only a very restricted set of comparisons may be excluded with a split dataset). In some embodiments, performance of each prediction is assessed within each predicted cell. In these embodiments, the sum of the number of channels used for compressed sensing and the number of channels used for the traditional approach does not exceed the technology's measurement capacity. For example, in one experimental embodiment described below, 4 mass channels are used to predict 8 markers. In this case, the 4 channels used in the compressed sensing experiment can be measured alongside the 8 channels needed for the standard experiment, since 8+4=12 is still within current measurement capability. This allows measurement of the markers both in the compressed version and the standard version simultaneously, allowing for assessment of prediction accuracy within the same cell. In some of these embodiments, it is helpful to use antibodies against different epitopes on each marker, to avoid reducing the signal in each cell due to competition effects. This kind of validation is especially useful for identifying subsampling that can be moved to a smaller cheaper device that is competent to do cell classification accurately with fewer labels than is used without compressed sensing.

Multiple Labels on Each Probe.

In certain embodiments, implementation of the compressed sensing approach allows for the use of multiple labels to detect multiple proteins. One way to implement this is to first attach a probe for marker 1 (e.g., an antibody for detecting protein 1) to each label (e.g., metal tag) to which marker 1 is assigned in the assignment matrix. Then, when performing the staining for an experiment, it is possible to add in each of the various labeled probes. An alternative, more advantageous approach is used in some embodiments. Rather than conjugate probe 1 to label 1 and separately conjugate another batch of probe 1 to label 2 also assigned to the same marker, it is possible to mix the two labels and directly label probe 1 with all labels to which marker 1 is assigned in the assignment matrix. This not only simplifies the labeling procedure of the probes by greatly reducing the number of required conjugations, but it also has the potential to equalize the amount of signal that each label contributes to the measurement for a given marker.

Equalizing Signal Ratios.

Typically, one searches for a binary value element when optimizing for the assignment matrix. In other words, the ratio of each marker between one of its assigned labels and another is exactly 1. In a reality, a ratio of 1 is not necessarily achievable. If it desired to control the ratio of signal of each marker on its various assigned labels, it is possible to do this without ever conjugating the label to probe and then measuring on stained cells. In certain embodiments, for example, a chelated polymer with label can be measured directly in the CyTOF, thereby allowing control of the signal ratios without additional cumbersome and time consuming steps of conjugations of labels to probes and cell staining, As an additional advantage, this approach offers a cost saving as no probes (e.g., antibodies) are needed.

Block Diagonals.

One way of stating the compressed sensing approach is to say that the approach provides the m non-negligible abundances of a possible M molecule types; or, simply "compress M into m". To assess whether the method is working it is advantageous to confine calibration experiments to conditions in which the M molecule types can be measured directly to see if indeed the m non negligible abundances produced by the approach agree with actual least negligible abundances. However if M molecule types cannot be measured in one experiment, in some embodiments, the calibration is performed using multiple experiments, each with fewer than M molecule types but different assignment matrices, and then the assignment matrices are combined. This approach is called block diagonals.

For embodiments in which two experiments can cover the M molecule types with direct measurements for calibration purposes, this is stated as follows. In order to compress M into m, instead N is compressed into n and P is compressed into p, where M=N+P. As a result, m=n+p. For example, to use 8 channels to predict 16 channels without 16 distinguishable labels (as in the case of fluorescent cytometry), instead of directly finding an 8→16 compressed sensing assignment matrix, instead two separate assignment matrices are determined. One assignment matrix compresses 8 out of the 16 desired markers into 4 channels, and another compresses the remaining 8 into another 4 channels. The channels do not overlap (e.g., the same patterns of 1 and 0 is not used in each column), and the marker need not overlay either (though they may, in some embodiments, if redundant measurements are desired).

This approach has at least two advantages in various embodiments. First, recall that in order to find the high performing assignment matrix, it is useful to start with a dataset in which all M markers have been measured. If such dataset is not available, or is beyond measurement capabilities and therefore cannot be made available, then the block diagonal design enables compression nonetheless, since the compression problem is broken into 2 or more smaller sub-problems. The second advantage comes from the fact that when implementing compressive sensing in the experimental setting, it is logistically more feasible to attach each marker to a smaller (rather than a larger) number of labels. The smaller the compressive sensing problem, the fewer the labels that are most useful. Thus, breaking down the problem into smaller sub-problems helps in experimentally implementing compressive sensing.

4. EXAMPLE EMBODIMENTS

To assess performance of the compressed sensing approach to cytometry, 31 channel CyTOF measurements were used as known relative abundances for 31 different human immune system cell receptor proteins. Computer (in silico) simulations of the method 300 were used to determine estimates of the 31 receptor relative abundances based on fewer than 31 channels. Example methods to estimate the assignment matrix and the parameter $\lambda$ were also demonstrated.

Thus, the compressed sensing approach described above was simulated by mixing (adding) signals from various labeled proteins in silico in accordance with an assignment matrix. The compressed sensing approach was then used to infer abundance values of each protein, and the original abundance values were used to assess the accuracy of the inferred values. For example, though 31 proteins were actually labeled with only one tag during the physical experiment, an assignment matrix is simulated by adding the signals from the various known protein abundances as if the proteins had been labeled according to the particular assignment matrix. The signals from these computed channels are then used with the assignment matrix and the procedure to minimize equation 2 to infer the relative abundance of the original proteins.

Since the goal is dimensionality increase, attempts were made to predict the 31 dimensions in the dataset using less than 31 simulated channels. For each round of prediction, a particular number less than 31 of simulated channels are made available for the compressed sensing computation. For the simulations, an assignment matrix was formulated. To ensure incoherence (i.e. randomness), the assignment matrix was generated using Bernoulli trials with p=0.5: each protein was included in a given channel with probability 0.5. Among the randomly generated assignment matrices, one or more favorable assignment matrices were chosen based on acceptable performance in one or more test populations. In addition, a value for $\lambda$ was chosen based on acceptable or optimized performance in test populations.

FIG. 5A and FIG. 5B and FIG. 5C are graphs that illustrate example agreement between actual abundances and abundances estimated using fewer labels and compressed sensing for three different proteins, respectively, according to various embodiments. Data are plotted for CyTOF measurements of 7200 cells were tested, 300 from each of 24 cell types; and indicate relative abundance. The inferred values were estimated by compressed sensing using Equation 2, a randomly generated assignment matrix A, $\lambda=1.6$, and measurements from only 24 of the 31 available channels (metal tag labels). Neither the assignment matrix A nor $\lambda$ were optimized for best performance.

FIG. 5A is a graph 500 for a 174-HLADR receptor, e.g., the protein HLADR was labeled with an antibody which had been conjugated to a metal tag of mass 174. The horizontal axis 502 is real abundance per cell (integrated counts per cell); and, the vertical axis 504 is inferred abundance per cell (integrated counts per cell). Each of the points 508 indicates the results for one cell. Because of the parameter $\lambda$, and the regularization penalty, several abundances were forced to zero, hence the noticeable concentration of points at inferred abundance of 0. Even though neither assignment matrix A nor $\lambda$ is optimized, there is a clear correlation between actual and inferred abundances.

FIG. 5B is a graph 520 for a 176-CD90 receptor. The horizontal axis 502 is the same as described above; and, the vertical axis 524 is inferred abundance per cell at a different scale than in FIG. 5A. Each of the points 528 indicates the results for one cell. This is a less favorable case with a tendency for many of the inferred values to overestimate the abundance of this receptor. FIG. 5C is a graph 540 for a 175-CXCR4 receptor. The horizontal axis 502 is the same as described above; and, the vertical axis 544 is inferred abundance per cell at a different scale than in FIG. 5A or FIG. 5B. Each of the points 548 indicates the results for one cell. This is an intermediate case with good correlation at the upper edge of an envelope encompassing the points, but a tendency for most of the inferred values to underestimate the abundance of this receptor.

Figure 6A:
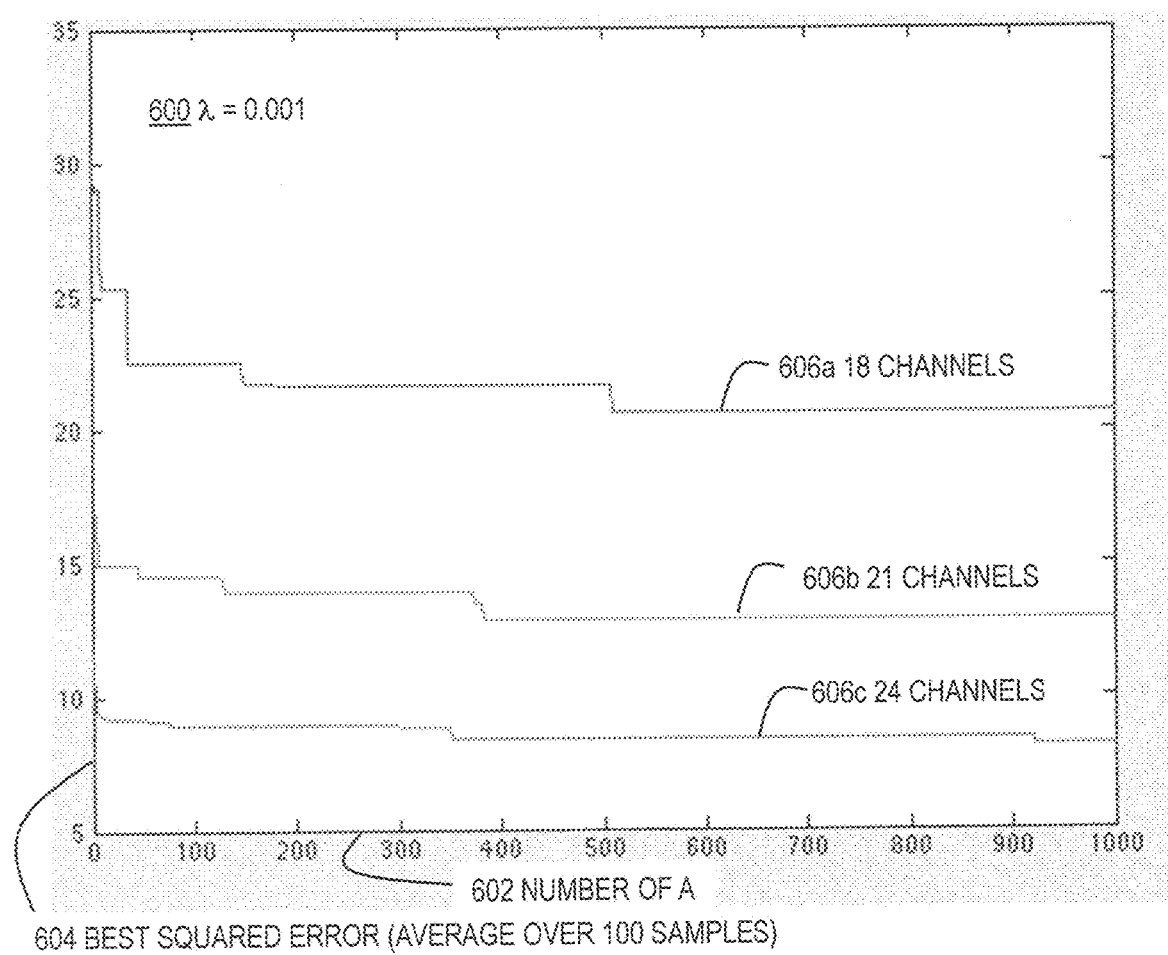
FIG. 6A and FIG. 6B and FIG. 6C are graphs that illustrate example improvement in performance with increase in number of trial assignment matrices, for three different values of λ, respectively, according to various embodiments.
Figure 6B:
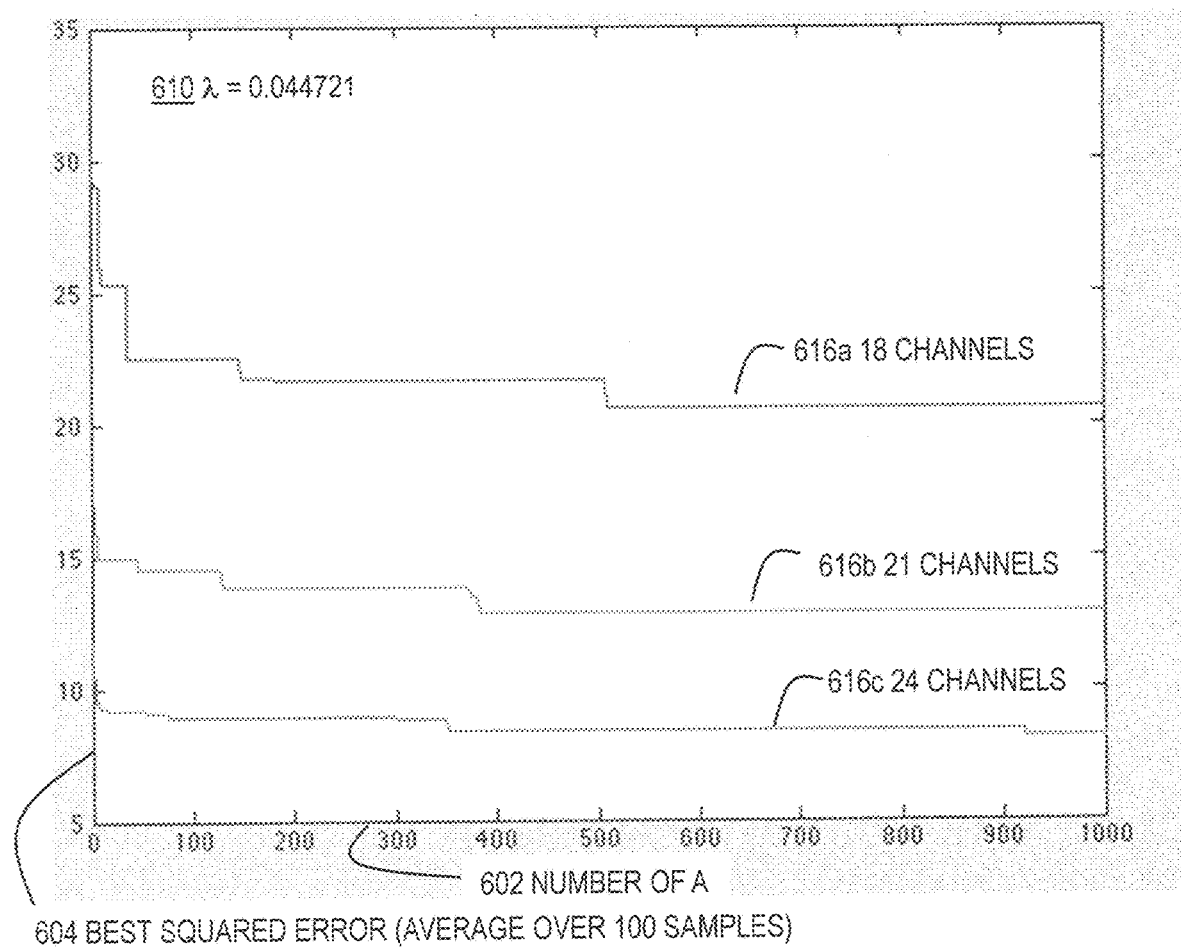
Figure 6C:
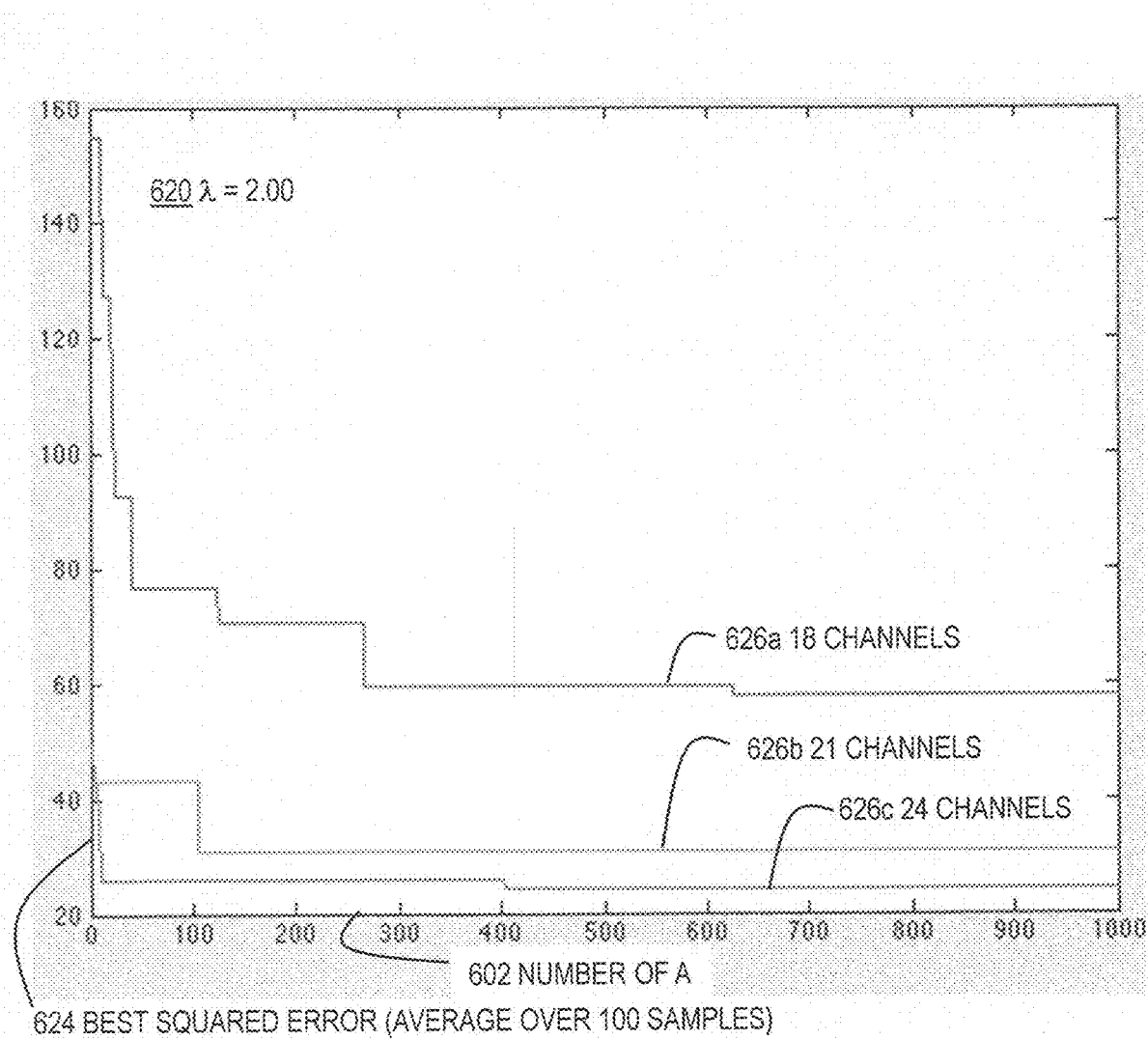

FIG. 6A and FIG. 6B and FIG. 6C are graph that illustrates example improvement in performance with increase in number of trial assignment matrices, for three different values of $\lambda$, respectively, according to various embodiments. To generate these plots, one thousand assignment matrices were produced with random values, as described above. CyTOF measurements of the abundances of 31 receptors on each of 100 cells (3100 measurements) were used to evaluate the relative performances of the assignment matrices.

FIG. 6A is a graph 600 that illustrates example results when the parameter $\lambda$ is negligible ($\lambda$=0.001). The horizontal axis 602 indicates the number (dimensionless) of assignment matrices considered. The vertical axis 604 indicates the squared difference (dimensionless) between the inferred abundances and the actual abundances averaged over the 3100 measurements for the one assignment matrix that gave the smallest difference among the assignment matrices considered. Trace 606a shows the results when the inferred values are based on 18 of the 31 channels (metal tag labels). As more assignment matrices are tried, a better performing assignment matrix is discovered. As each superior assignment matrix is found in turn, the smallest error, indicated by trace 606a, drops. By the time about 600 assignment matrices are tried, the best performing matrix performs about as well as any other matrix later found.

Trace 606b shows the results when the inferred values are based on 21 of the 31 channels (metal tag labels). Trace 606c shows the results when the inferred values are based on 24 of the 31 channels (metal tag labels). As expected, the more channels included, the better is the error of the best performing assignment matrix; but, the trends are similar. By the time about 600 assignment matrices are tried, the best performing matrix performs about as well as any other matrix later found in this embodiment.

FIG. 6B is a graph 610 that illustrates example results when the parameter $\lambda$ is small but not negligible ($\lambda$=0.044721). The horizontal axis 602 and vertical axis 604 are as described above. Trace 616a shows the results when the inferred values are based on 18 of the 31 channels (metal tag labels). Trace 616b shows the results when the inferred values are based on 21 of the 31 channels (metal tag labels). Trace 616c shows the results when the inferred values are based on 24 of the 31 channels (metal tag labels). The results are almost identical to those of FIG. 6A. By the time about 600 assignment matrices are tried, the best performing matrix performs about as well as any other matrix later found; and, the more channels included, the better is the error of the best performing assignment matrix.

FIG. 6C is a graph 610 that illustrates example results when the parameter $\lambda$ is large ($\lambda$=2.00). The horizontal axis 602 is as described above. The vertical axis 624 again indicates the squared difference (dimensionless) between the inferred abundances and the actual abundances averaged over the 3100 measurements for the one assignment matrix that gave the smallest difference among the assignment matrices considered; but, the errors are much larger so the vertical axis 624 extends to much larger values. Trace 626a shows the results when the inferred values are based on 18 of the 31 channels (metal tag labels). Trace 626b shows the results when the inferred values are based on 21 of the 31 channels (metal tag labels). Trace 626c shows the results when the inferred values are based on 24 of the 31 channels (metal tag labels). Even though the errors are much larger, the trends are similar to those described above. By the time about 600 assignment matrices are tried, the best performing matrix performs about as well as any other matrix later found; and, the more channels included, the better is the error of the best performing assignment matrix.

FIG. 6A though FIG. 6C demonstrate that with an appropriate one or more test data sets that describes the cytometry regime of interest, a best assignment matrix can be discovered by a brute force approach of randomly generating hundreds of assignment matrices and determining which assignment matrix gives the best performance. Such an approach is allowed in method 300 by the loop indicated by steps 309 through step 317 and including step 315. For example, multiple random assignment matrices can be determined for 60 proteins and 31 channels (e.g., as depicted in FIG. 2) and then tested against multiple CyTOF experiments that provide actual abundances of 31 proteins at a time.

Figure 7A:
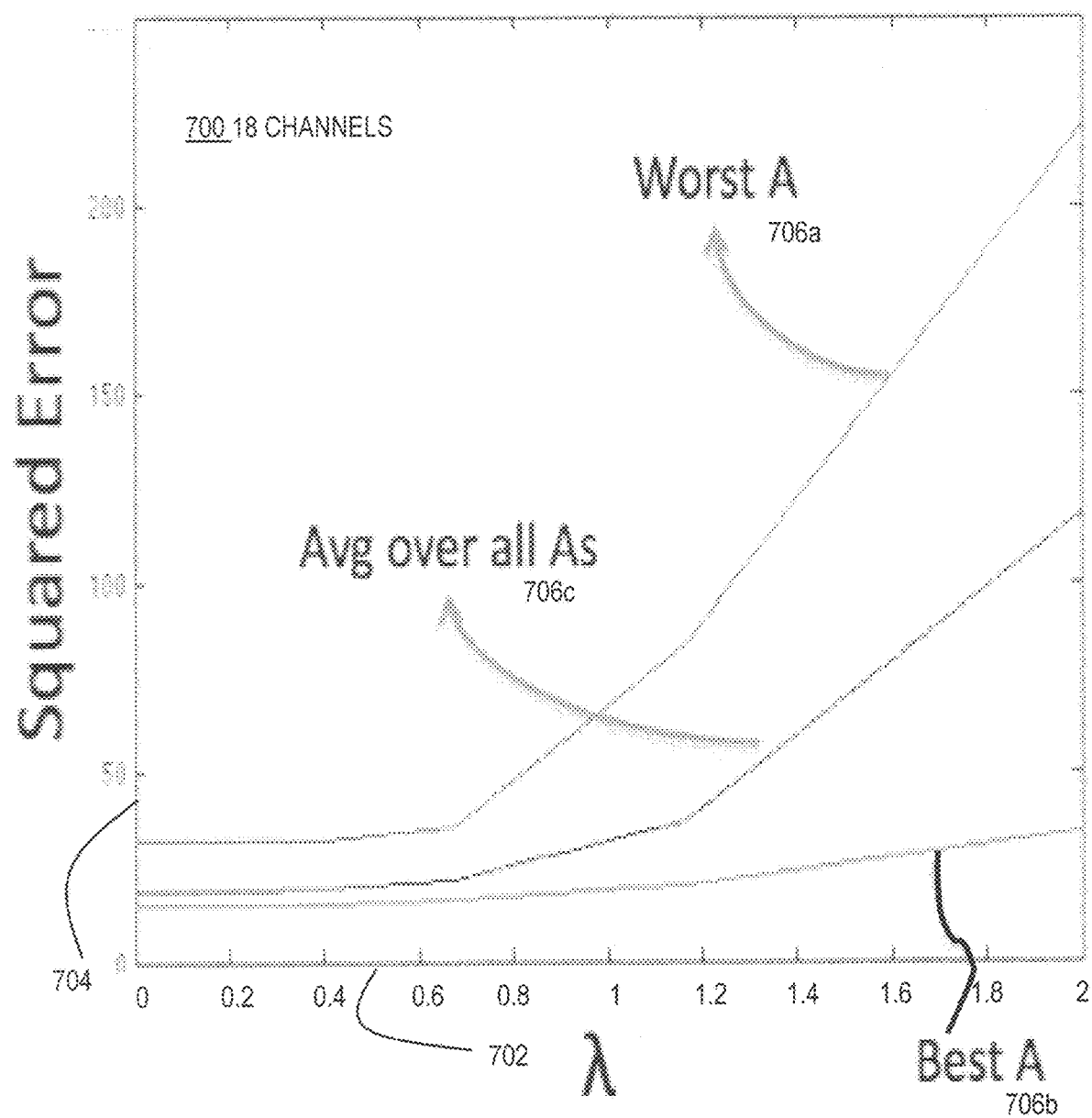
FIG. 7A is a graph that illustrates an example dependence of performance on choice of assignment matrix A, according to various embodiments.

FIG. 7A is a graph 700 that illustrates an example dependence of performance on choice of assignment matrix A, according to various embodiments. The horizontal axis 702 indicates values for $\lambda$ (dimensionless). The vertical axis 704 indicates the squared difference (dimensionless) between the inferred abundances and the actual abundances averaged over the 3100 measurements. Trace 706a indicates the result for the assignment matrix ("Worst A") that gave the largest error, as a function of $\lambda$. Trace 706b indicates the result for the assignment matrix ("Best A") that gave the smallest error, as a function of $\lambda$. Trace 706c indicates the average error over all assignment matrices considered (about 1000), as a function of $\lambda$. The selection of an assignment matrices is seen to have a dramatic effect on the accuracy of the predictions, with the best matrix demonstrating drastically lower error than the worst. It is also shown that smaller values of $\lambda$ can reduce the range of errors that depend on the assignment matrix chosen.

Figure 7B:
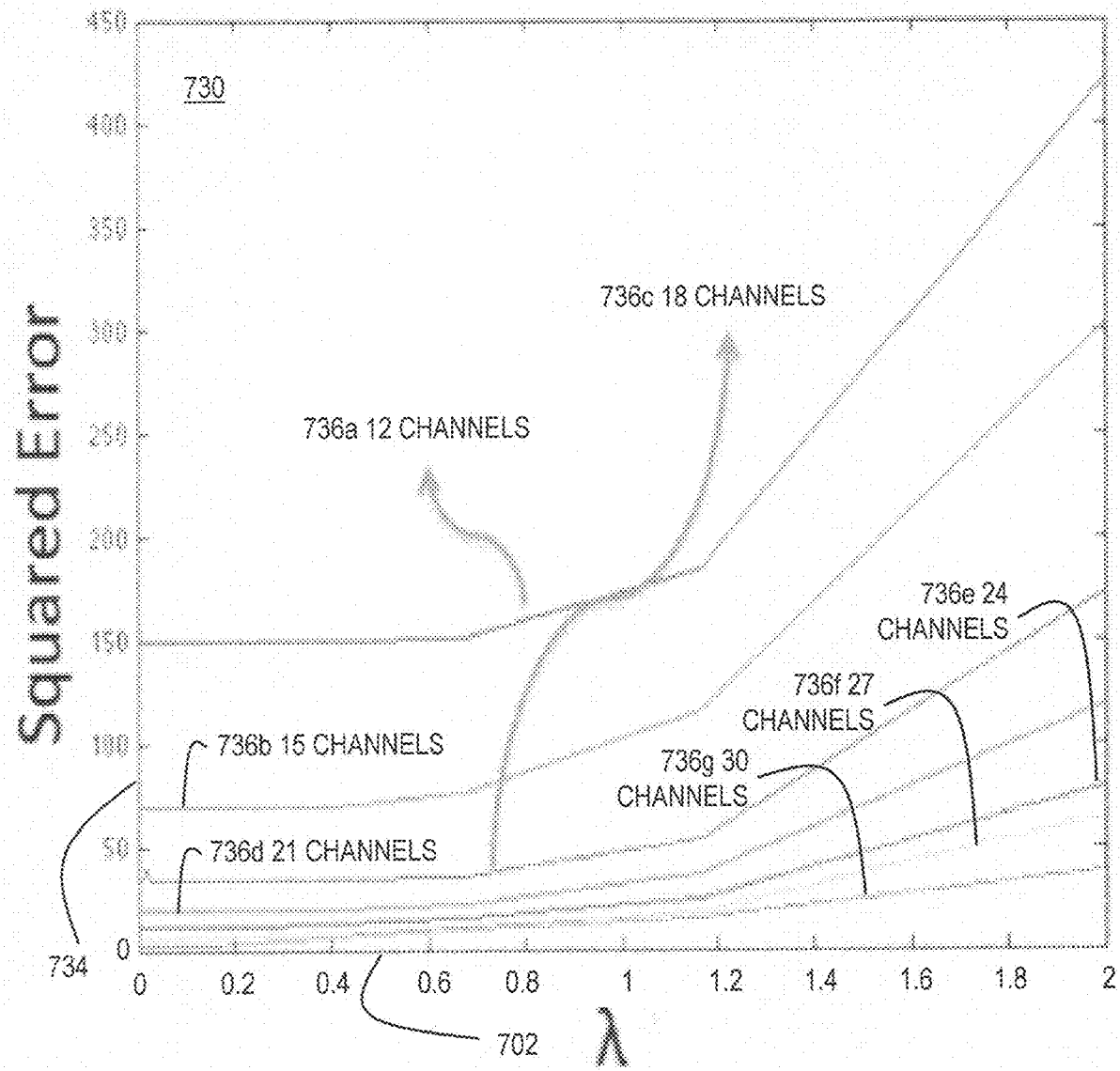
FIG. 7B is a graph that illustrates an example of improved performance of compressed sensing estimate of abundance with values of λ less than about 1.0, according to various embodiments.

FIG. 7B is a graph 730 that illustrates an example of improved performance of compressed sensing estimate of abundance with values of $\lambda$ less than about 1.0, according to various embodiments. The horizontal axis 702 is the same as in FIG. 7A. The vertical axis 734 indicates the squared difference (dimensionless) between the inferred abundances and the actual abundances averaged over the 3100 measurements with an expanded range to larger errors than in FIG. 7A. Traces 736a through 736g show the results for an increasing number of channels from 12 to 30 in increments of 3, respectively, for a randomly generated assignment matrix and a range of $\lambda$. Based on the effect of $\lambda$ values over various channel numbers, it is concluded that $\lambda$ is advantageously selected to be 1 or smaller (while remaining greater than 0) to ensure accurate predictions, at least for this test dataset.

To assess the impact of various prediction error levels, a decision tree classifier was built using human-labeled (e.g., gated) cell types. Once a cell's receptor abundance values are predicted by compressed sensing, the classifier determines the likelihood that the cell will be misclassified because of the abundance errors in the inferred values. Substantively, classification error demonstrates the impact of the simple squared deviation from actual value that is shown in FIG. 7A and FIG. 7B, described above. Using 31 dimensional CyTOF data for known values and protein abundances inferred from fewer channels and compressed sensing, the trained classifier was executed to ascertain the classification of a cell based on its inferred abundance values and its correct classification based on the full 31 dimensional CyTOF data. If a cell is classified based on its inferred abundances differently from its classification based on its actual abundances, then a classification error is counted. The classification accuracy was determined for number of channels ranging from 16 to 22 and including 31 channels for reference. Results are determined for optimized λ and assignment matrix, as well as non-optimized λ and assignment matrix A as listed in Table 1. In the optimized case, greater than 95% classification accuracy is achieved using 19 channels. This suggests that the method is able to properly classify a cell over 80% of the time with nearly double the number of protein abundances inferred from the 31 metal tags of CyTOF measurements.

TABLE 1

Classification accuracy using compressed sensing for cytometry.

| Experiment | 1 (control) | 2 | 3 | 4 |
|---|---|---|---|---|
| Channels used | 31 | 22 | 19 | 16 |
| Classification accuracy (%) - non optimized λ | 100 | 88 | 77 | 70 |
| Classification accuracy (%) - non optimized A | 100 | 91 | 80 | 82 |
| Classification accuracy (%) - optimized λ, A | 100 | 97 | 89 | 82 |

Wet Validation for One 4→8 Matrix.

One high performing 4×8 assignment matrix based on the simulations was selected and implemented in the laboratory for characterizing actual cells. The protocols are described below. First, a high performing matrix was selected. FIG. 10 illustrates a selected example assignment matrix for validation experiment using four mass labels for eight protein markers CD19, CD4, CD8, CD61, CD45RA, CD14, CD15 and CD3, according to an embodiment. Next, conjugations in accordance with the assignments in the matrix were performed, such that each protein is detected by a set of antibodies which have been labeled by the metal labels according to the matrix assignments. Next, PBMC (peripheral blood mononuclear cells) were stained with: (i) 4 distinct metals in accordance with the assignment matrix of FIG. 10; (ii) a regular 8-metal stain as a gold standard for comparison to the compressed sensing results; and (iii) each protein individually using the same antibody concentrations as those used in the compressed experiment thereby allowing for quantification of the relative signal strength of the protein on each of the metals with which it is labeled. The proteins measured were the markers CD19, CD4, CD8, CD61, CD45RA, CD14, CD16 and CD3, and the metals used were had masses 160, 165, 169 and 174.

Figure 11A:
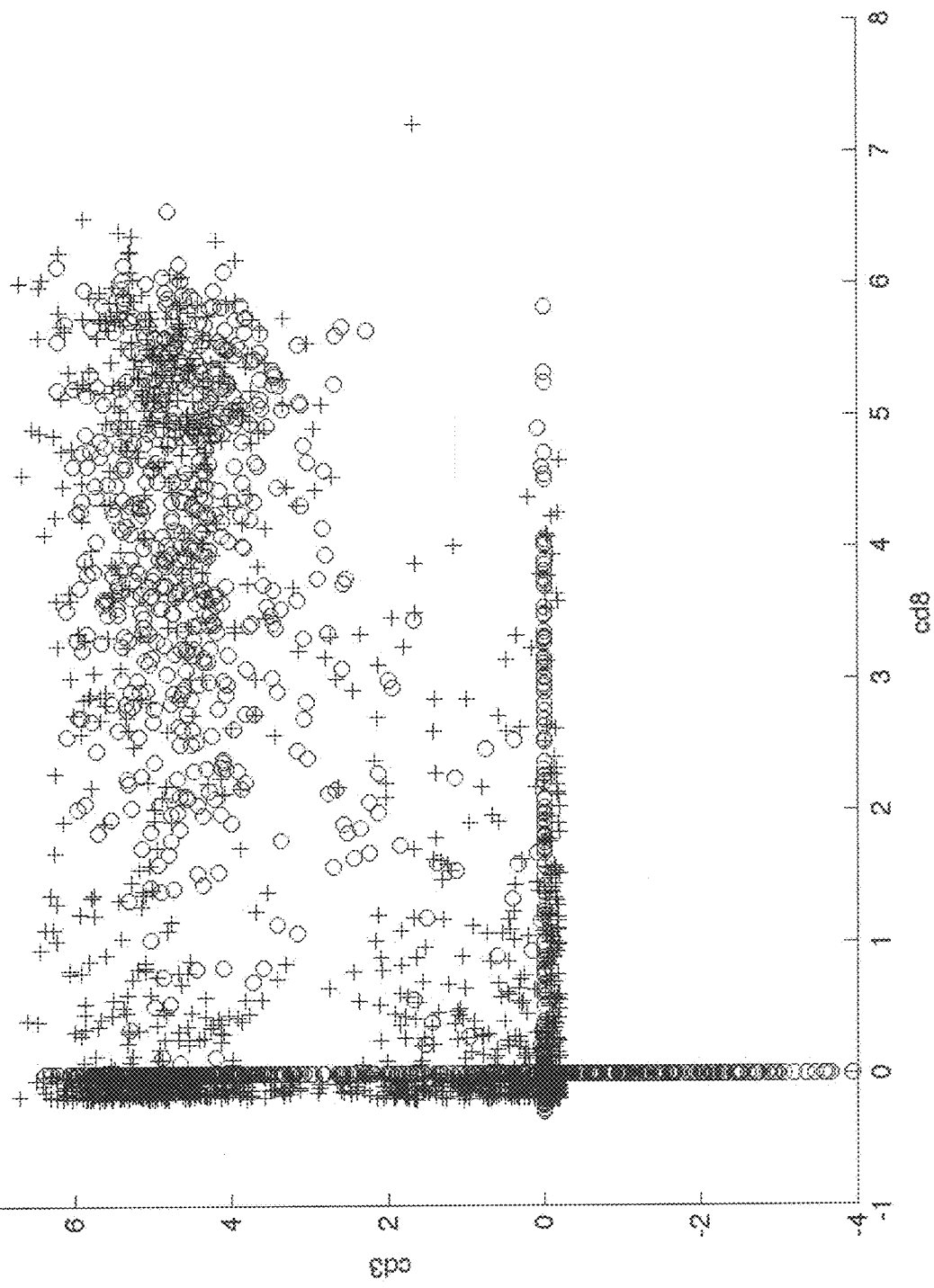

Visual inspection of original (uncompressed) data (also called raw data herein) overlaid with data that had been predicted by compressed sensing showed clearly that the approach worked. FIGS. 11A and 11B are a scatter plots that illustrate example agreement of raw and predicted values of markers, two at a time, using the assignment matrix of FIG. 10, according to an embodiment. FIG. 11A is a scatter plot 1100 of number of cells having relative abundances of CD8 given by the horizontal axis 1102 and CD3 given by the vertical axis 1104. Raw values based on eight labels are given by plus symbols and predicted values based on compressed sensing and only four labels by open circles. The population clusters are centered on substantively similar relative values and fall off at substantively similar rates and orientations. In some comparisons, prior knowledge is used to eliminate unrealistic predictions. For example, CD 19 is known to be mutually exclusive with CD3. FIG. 11B is a scatter plot 1120 of number of cells having relative abundances of CD19 given by the horizontal axis 1122 and CD3 given by the vertical axis 1124. Raw values based on eight labels are given by plus symbols and predicted values based on compressed sensing and only four labels by open circles. Absent information about mutual exclusivity, the compressed sensing solution allows a population cluster with both proteins present. Adding constraints to the solution would eliminate this cluster. Similarly, adding constraint to prevent negative abundances would eliminate cluster. After applying such constraints the raw and predicted clusters are in much better agreement.

FIG. 12 is a bar graph 1200 that illustrates example agreement in raw and predicted cell type classification, using the assignment matrix of FIG. 10, according to an embodiment. The horizontal axis 1202 indicates cell type and the vertical axis 1204 indicates relative frequency. Raw values based on eight labels are given by the second bar 1208 for each cell type, and predicted values based on compressed sensing and only four labels are given by the first bar 1206. These data were manually gated but using boundaries as established by the raw plots. CD45RA is noisy and leads to no predicted Naïve TH cells in this run. The relative frequencies of the different cell type classifications are substantively similar.

Matrices Found for 3→6 and 5→10.

Multiple matrices for both kinds of compression were found during simulations. It is desirable to use matrices that give two dimensional contour plots with predicted contours that overlay perfectly with the original (raw) contours from with the compressed sensing results were simulated, as found for the high-performing 4×8 assignment matrix of FIG. 10. In order to automatically detect the matrices which give good overlaid contour plots, it was found that an advantageous approach is a combination of goodness of fit metrics, including mean square error, classification accuracy (when a classifier is used) and the $\ell_1$ norm distance of all pairwise plots, distance of predicted from original data. We have also generated distributions of matrix performance scores. We find that the distributions have a large number of high scoring matrices and fewer poor scoring ones. Thus most matrices provide adequate results. A matrix found to give good results in a test case with a gold standard or other trustworthy calibration data is likely to give good results for similar markers and number of labels. In some embodiments, distances of predicted values from a center of a cluster of predicted values can be used in lieu of distance from a calibration value.

Figure 13A:
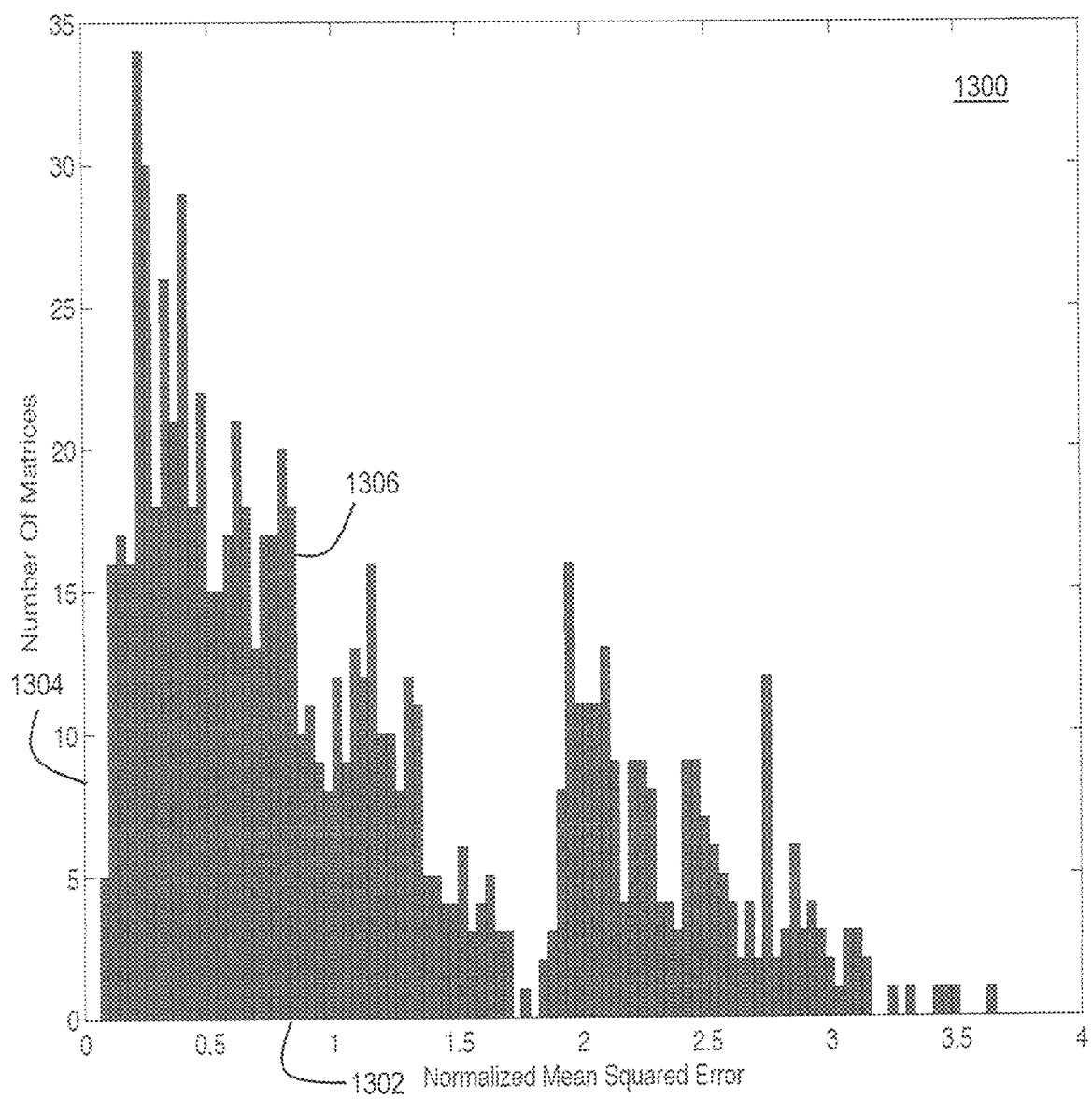
FIGS. 13A and 13B are graphs that illustrate example distributions of errors of predicted values of six markers based on three labels using different 3×6 assignment matrices, according to various embodiments; and, FIG. 14 is a graph that illustrates example distribution of errors of predicted values of ten markers based on five labels using different 5×10 assignment matrices, according to various embodiments.
Figure 13B:
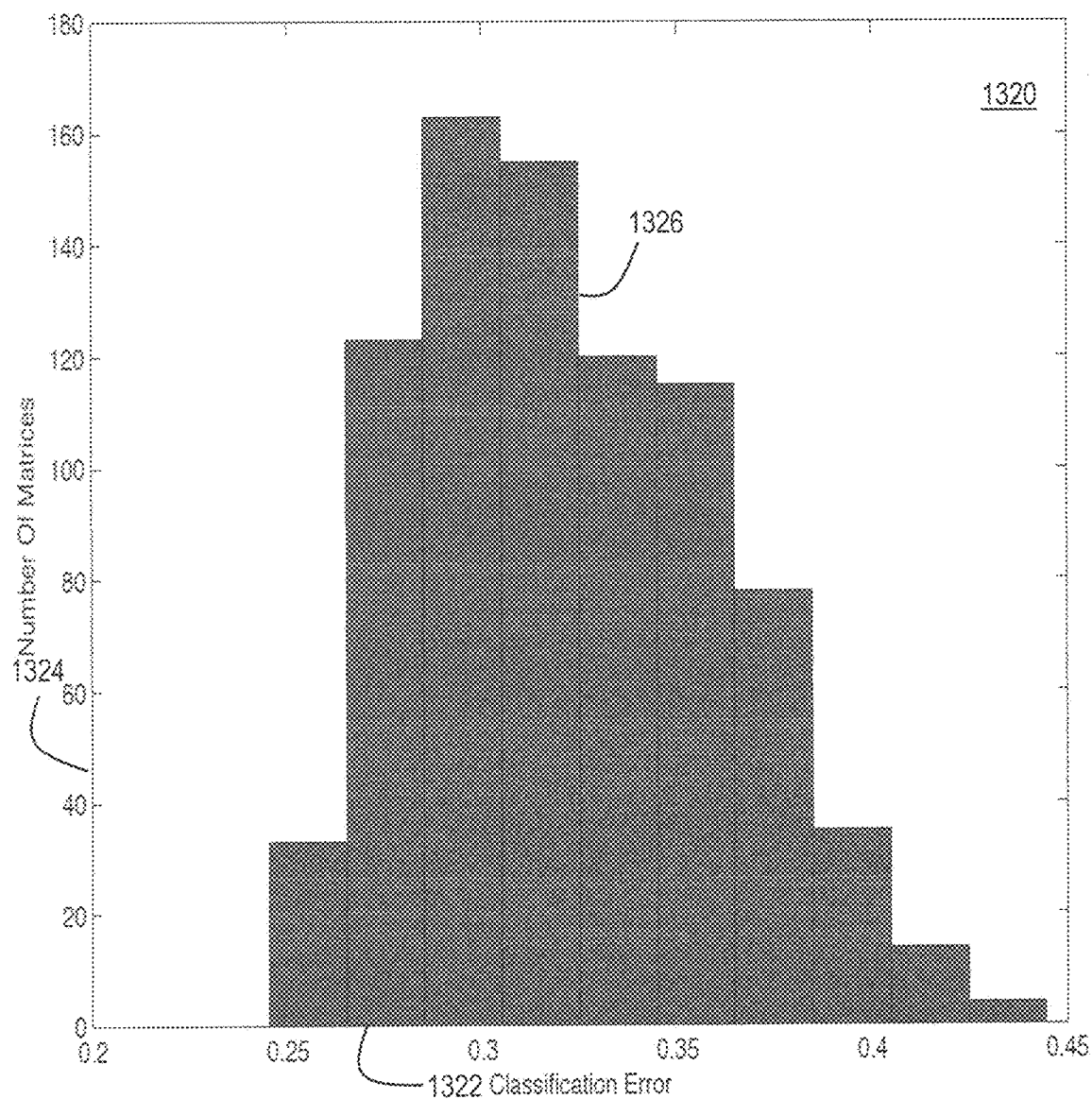

FIGS. 13A and 13B are graphs that illustrate example distributions of errors of predicted values of six markers based on three labels using different 3×6 assignment matrices, according to various embodiments. The six markers in the data set used as the basis for these simulations were CD4, CD8, CD19, CD14, CD11c and CD16.

FIG. 13A is a bar graph 1300 that illustrates an example distribution 1306 of normalized mean squared error between the 6 dimensional value of the raw data and the 6 dimensional values provided by each of thousands of 3×6 assignment matrices. The horizontal 1302 axis is normalized mean squared error and the vertical axis 1304 is the number of matrices with that error. Smaller errors are populated by the largest numbers of matrices. FIG. 13B is a bar graph 1320 that illustrates an example distribution 1326 of classification error score between classes based on the raw data and classes based on the predicted values for a large number of matrices. Most matrices behave well for classification. An example matrix is as follows:

| 5 × 10 | | | | | | | | | |
|---|---|---|---|---|---|---|---|---|---|
| cd3 | cd4 | cd8 | cd45ra | cd19 | hla-dr | cd16 | cd11c | cd33 | cd14 |
| 1 | 1 | 1 | 1 | 0 | 0 | 1 | 0 | 0 | 0 |
| 0 | 1 | 1 | 1 | 1 | 0 | 0 | 0 | 1 | 1 |
| 1 | 0 | 0 | 1 | 1 | 1 | 0 | 0 | 0 | 0 |
| 1 | 0 | 0 | 0 | 0 | 1 | 0 | 1 | 0 | 1 |
| 0 | 1 | 0 | 1 | 0 | 1 | 1 | 1 | 1 | 0 |

Figure 14:
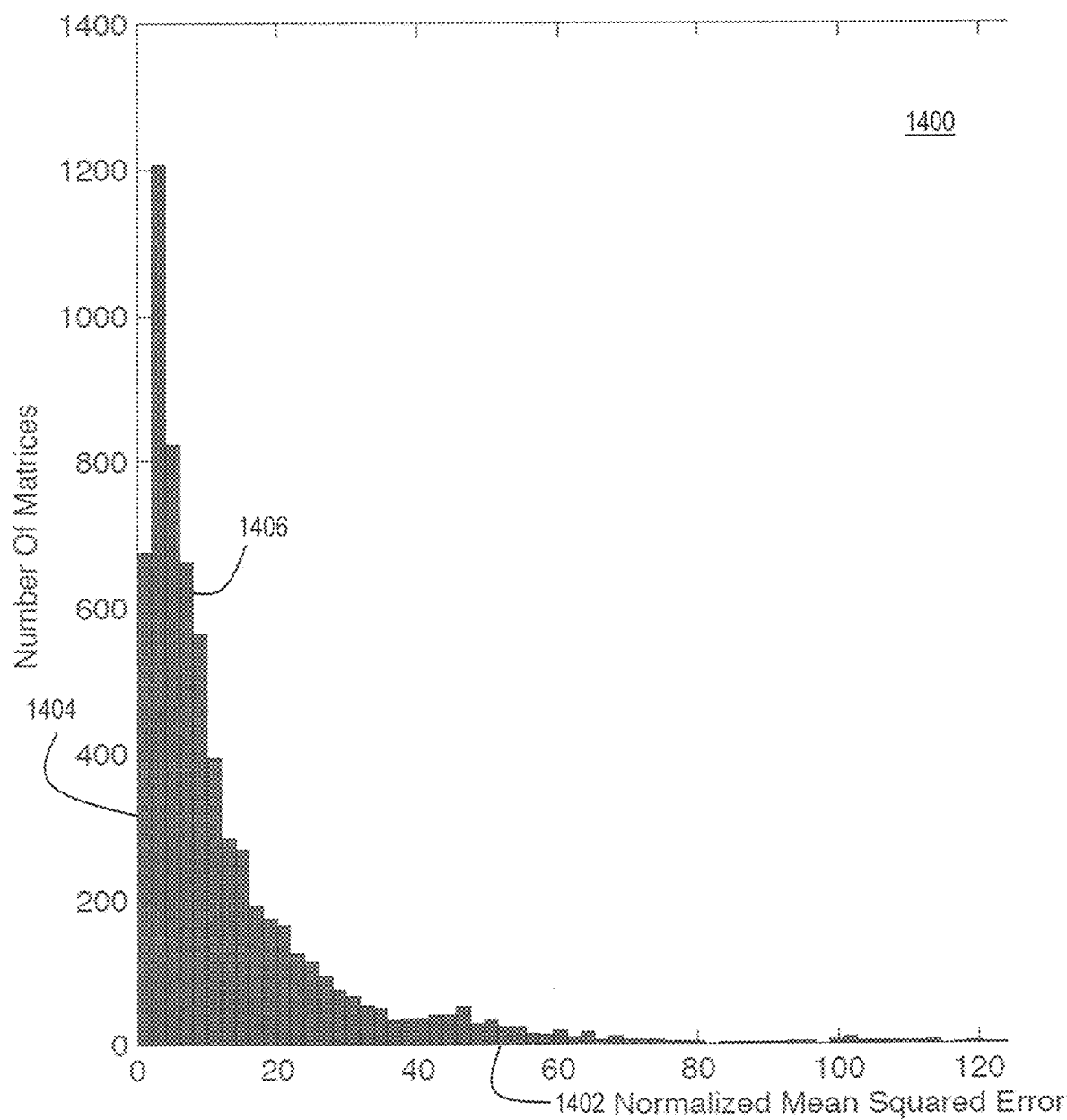

For matrices used to compress 10 markers using only 5 labels, similar results were obtained. FIG. 14 is a graph 1400 that illustrates example distribution 1406 of errors of predicted values of ten markers based on five labels using thousands of different 5×10 assignment matrices, according to various embodiments. The ten markers in the data set used as the basis for these simulations were CD3, CD4, CD8, D45RA, CD19, HLA-DR, CD11c, CD14, CD16 and CD33. The horizontal axis 1402 is normalized mean squared error and the vertical axis 1404 is the number of matrices with that error. Much larger errors occur than in FIG. 13A; however, again the smaller errors are populated by the largest numbers of matrices. An example matrix is above.

| 3 × 6 | | | | | |
|---|---|---|---|---|---|
| cd4 | cd8 | cd19 | cd14 | cd11c | cd16 |
| 1 | 0 | 0 | 1 | 1 | 0 |
| 1 | 1 | 0 | 0 | 1 | 1 |
| 1 | 1 | 1 | 0 | 0 | 0 |

5. EXAMPLE MATERIALS AND METHODS

Cells and reagents for bead surrogates. A single lot of polystyrene bead standards embedded with five different metal isotopes (La 139, Pr 141, Tb 159, Tm 169, and Lu 175) having masses spanning the primary analysis range of the mass cytometer were synthesized as described in Abdelrahman, A. I., et al., "Metal-Containing Polystyrene Beads as Standards for Mass Cytometry," *Journal of analytical atomic spectrometry*, v 25, no. 3 pp. 260-268, 2010 and Abdelrahman, A. I., et al., "Lanthanide-containing polymer microspheres by multiple-stage dispersion polymerization for highly multiplexed bioassays," *Journal of the American Chemical Society*, v 131, no. 42: p. 15276-83, 2009, and provided by Scott Tanner's group at the University of Toronto. These polystyrene bead standards were selected such that the median dual counts on each mass channel ranged between 100 and 2000 counts per bead to ensure that there was both sufficient signal over background and that the signal was within the linear measurement range of the instrument. Antibodies against cell human blood cell surface epitopes were purchased from DVS Sciences (Sunnyvale, Calif.): CD19-Nd142, CD4-Nd145, CD8-Nd146, CD20-Sm147, CD61-Gd150, CD123-Eu151, CD45RA-Eu153, CD45-Sm154, CD33-Gd158, CD11c-159Th, CD14-Dy160, CD16-Ho165, CD38-Er167, CD3-Yb170. Human peripheral blood mononuclear cells (PBMCs) were Ficoll purified from whole blood obtained from the Stanford Blood Bank as described in Bandura, D. R., et al., "Mass Cytometry: Technique for Real Time Single Cell Multitarget Immunoassay Based on Inductively Coupled Plasma Time-of-Flight Mass Spectrometry," *Anal Chem*, 2009.

Preparation of Cellular Samples with Bead Standards.

PBMCs were stained as described in Bandura, 2009. Briefly, 1.6% paraformaldehyde (PFA) fixed PBMCs were stained simultaneously with metal-conjugated antibodies according to the manufacturer's recommendation. Cells were then permeabilized and fixed with methanol and incubated with a 1:5000 dilution of the Ir intercalator (2000× formulation, DVS Sciences) in PBS with 1.6% PFA. Cells were stored in this format for up to 1 month at 4° C. Over that period, aliquots of cells were periodically removed and analyzed on the same CyTOF mass cytometer (DVS Sciences). Just prior to analysis, the stained and intercalated cell pellet was re-suspended to a concentration of approximately 106 cells per mL in ddH2O containing the bead standard at a concentration ranging between 1 and 2×104 beads per mL. Ideally, the bead standard acquisition rate should be 3 to 6 beads per second. The bead standards were prepared immediately prior to analysis, and the mixture of beads and cells were filtered through a 35-μm filter cap FACS tubes (BD Biosciences) before analysis.

Preparation of Cellular Samples with Actual Cells.

PBMCs were stained as previously described in Bendall, S. C., et al. Briefly, 1.6% paraformaldehyde (PFA) fixed PBMCs were stained simultaneously with metal-conjugated antibodies according to the manufacturer's recommendation. Cells were then permeabilized and fixed with methanol and incubated with a 1:5000 dilution of the Ir intercalator (2000× formulation, DVS Sciences) in PBS with 1.6% PFA. Cells were analyzed on a CyTOF mass cytometer (DVS Sciences). Just prior to analysis, the stained and intercalated cell pellet was re-suspended to a concentration of approximately $10^6$ cells per mL in ddH$_2$O containing a bead standard at a concentration ranging between 1 and 2×10$^4$ beads per mL.

Data Acquisition.

Cell events were collected on a CyTOF mass cytometer as described in Bandura, 2009. To ensure maximum consistency across data files, the dual count conversion was performed using 'instrument' mode rather than 'data' mode. Along with standard instrument maintenance and tuning, the instrument dual count slopes were also calibrated weekly according to the manufacturer's recommended protocol. The instrument was cleaned and tuned between the third and fourth acquisitions. All other data acquisition and fcs conversion parameters were the manufacturer's default settings. Files generated by instruments used in flow cytometry (FCM) experiments are in binary format and cannot be directly processed by independent analysis and visualization software. Reading and transforming a binary .fcs file requires understanding FCS file formats including FCS2.0 and FCS3.0. Unlike FCS2.0 which usually stores log-transformed data, FCS3.0 files keep the original raw outputs from the instrument in a linear mode. Analysis and visualization software needs to transform the linear-mode data before delivering the data to biologists The data were processed, including normalization and visualization, using MATLAB (from MathWorks of Natick, Mass.).

6. CONTROLLER HARDWARE OVERVIEW

FIG. 8 is a block diagram that illustrates a computer system 800 upon which an embodiment of the invention may be implemented. Computer system 800 includes a communication mechanism such as a bus 810 for passing information between other internal and external components of the computer system 800. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 800, or a portion thereof, constitutes a means for performing one or more steps of one or more methods described herein.

A sequence of binary digits constitutes digital data that is used to represent a number or code for a character. A bus 810 includes many parallel conductors of information so that information is transferred quickly among devices coupled to the bus 810. One or more processors 802 for processing information are coupled with the bus 810. A processor 802 performs a set of operations on information. The set of operations include bringing information in from the bus 810 and placing information on the bus 810. The set of operations also typically include comparing two or more units of information, shifting positions of units of information, and combining two or more units of information, such as by addition or multiplication. A sequence of operations to be executed by the processor 802 constitute computer instructions.

Computer system 800 also includes a memory 804 coupled to bus 810. The memory 804, such as a random access memory (RAM) or other dynamic storage device, stores information including computer instructions. Dynamic memory allows information stored therein to be changed by the computer system 800. RAM allows a unit of information stored at a location called a memory address to be stored and retrieved independently of information at neighboring addresses. The memory 804 is also used by the processor 802 to store temporary values during execution of computer instructions. The computer system 800 also includes a read only memory (ROM) 806 or other static storage device coupled to the bus 810 for storing static information, including instructions, that is not changed by the computer system 800. Also coupled to bus 810 is a non-volatile (persistent) storage device 808, such as a magnetic disk or optical disk, for storing information, including instructions, that persists even when the computer system 800 is turned off or otherwise loses power.

Information, including instructions, is provided to the bus 810 for use by the processor from an external input device 812, such as a keyboard containing alphanumeric keys operated by a human user, or a sensor. A sensor detects conditions in its vicinity and transforms those detections into signals compatible with the signals used to represent information in computer system 800. Other external devices coupled to bus 810, used primarily for interacting with humans, include a display device 814, such as a cathode ray tube (CRT) or a liquid crystal display (LCD), for presenting images, and a pointing device 816, such as a mouse or a trackball or cursor direction keys, for controlling a position of a small cursor image presented on the display 814 and issuing commands associated with graphical elements presented on the display 814.

In the illustrated embodiment, special purpose hardware, such as an application specific integrated circuit (IC) 820, is coupled to bus 810. The special purpose hardware is configured to perform operations not performed by processor 802 quickly enough for special purposes. Examples of application specific ICs include graphics accelerator cards for generating images for display 814, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 800 also includes one or more instances of a communications interface 870 coupled to bus 810. Communication interface 870 provides a two-way communication coupling to a variety of external devices that operate with their own processors, such as printers, scanners and external disks. In general the coupling is with a network link 878 that is connected to a local network 880 to which a variety of external devices with their own processors are connected. For example, communication interface 870 may be a parallel port or a serial port or a universal serial bus (USB) port on a personal computer. In some embodiments, communications interface 870 is an integrated services digital network (ISDN) card or a digital subscriber line (DSL) card or a telephone modem that provides an information communication connection to a corresponding type of telephone line. In some embodiments, a communication interface 870 is a cable modem that converts signals on bus 810 into signals for a communication connection over a coaxial cable or into optical signals for a communication connection over a fiber optic cable. As another example, communications interface 870 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 870 sends and receives electrical, acoustic or electromagnetic signals, including infrared and optical signals, that carry information streams, such as digital data.

The term computer-readable medium is used herein to refer to any medium that participates in providing information to processor 802, including instructions for execution. Such a medium may take many forms, including, but not limited to, non-volatile media, volatile media and transmission media. Non-volatile media include, for example, optical or magnetic disks, such as storage device 808. Volatile media include, for example, dynamic memory 804. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 802, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 802, except for carrier waves and other signals.

Logic encoded in one or more tangible media includes one or both of processor instructions on a computer-readable storage media and special purpose hardware, such as ASIC 820.

Network link 878 typically provides information communication through one or more networks to other devices that use or process the information. For example, network link 878 may provide a connection through local network 880 to a host computer 882 or to equipment 884 operated by an Internet Service Provider (ISP). ISP equipment 884 in turn provides data communication services through the public, world-wide packet-switching communication network of networks now commonly referred to as the Internet 890. A computer called a server 892 connected to the Internet provides a service in response to information received over the Internet. For example, server 892 provides information representing video data for presentation at display 814.

The invention is related to the use of computer system 800 for implementing the techniques described herein. According to one embodiment of the invention, those techniques are performed by computer system 800 in response to processor 802 executing one or more sequences of one or more instructions contained in memory 804. Such instructions, also called software and program code, may be read into memory 804 from another computer-readable medium such as storage device 808. Execution of the sequences of instructions contained in memory 804 causes processor 802 to perform the method steps described herein. In alternative embodiments, hardware, such as application specific integrated circuit 820, may be used in place of or in combination with software and general processor to implement the invention. Thus, embodiments of the invention are not limited to any specific combination of hardware and software with processor.

The signals transmitted over network link 878 and other networks through communications interface 870, carry information to and from computer system 800. Computer system 800 can send and receive information, including program code, through the networks 880, 890 among others, through network link 878 and communications interface 870. In an example using the Internet 890, a server 892 transmits program code for a particular application, requested by a message sent from computer 800, through Internet 890, ISP equipment 884, local network 880 and communications interface 870. The received code may be executed by processor 802 as it is received, or may be stored in storage device 808 or other non-volatile storage for later execution, or both. In this manner, computer system 800 may obtain application program code in the form of a signal on a carrier wave.

Various forms of computer readable media may be involved in carrying one or more sequence of instructions or data or both to processor 802 for execution. For example, instructions and data may initially be carried on a magnetic disk of a remote computer such as host 882. The remote computer loads the instructions and data into its dynamic memory and sends the instructions and data over a telephone line using a modem. A modem local to the computer system 800 receives the instructions and data on a telephone line and uses an infra-red transmitter to convert the instructions and data to a signal on an infra-red a carrier wave serving as the network link 878. An infrared detector serving as communications interface 870 receives the instructions and data carried in the infrared signal and places information representing the instructions and data onto bus 810. Bus 810 carries the information to memory 804 from which processor 802 retrieves and executes the instructions using some of the data sent with the instructions. The instructions and data received in memory 804 may optionally be stored on storage device 808, either before or after execution by the processor 802.

FIG. 9 illustrates a chip set 900 upon which an embodiment of the invention may be implemented. Chip set 900 is programmed to perform one or more steps of a method described herein and includes, for instance, the processor and memory components described with respect to FIG. 8 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 900, or a portion thereof, constitutes a means for performing one or more steps of a method described herein.

In one embodiment, the chip set 900 includes a communication mechanism such as a bus 901 for passing information among the components of the chip set 900. A processor 903 has connectivity to the bus 901 to execute instructions and process information stored in, for example, a memory 905. The processor 903 may include one or more processing cores with each core configured to perform independently. A multi-core processor enables multiprocessing within a single physical package. Examples of a multi-core processor include two, four, eight, or greater numbers of processing cores. Alternatively or in addition, the processor 903 may include one or more microprocessors configured in tandem via the bus 901 to enable independent execution of instructions, pipelining, and multithreading. The processor 903 may also be accompanied with one or more specialized components to perform certain processing functions and tasks such as one or more digital signal processors (DSP) 907, or one or more application-specific integrated circuits (ASIC) 909. A DSP 907 typically is configured to process real-world signals (e.g., sound) in real time independently of the processor 903. Similarly, an ASIC 909 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 903 and accompanying components have connectivity to the memory 905 via the bus 901. The memory 905 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 905 also stores the data associated with or generated by the execution of one or more steps of the methods described herein.

6. ALTERNATIVES AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A method comprising:
physically labeling a plurality of M different biological molecule types in a biological sample, each different biological molecule type with a unique combination of a plurality of labels, according to an assignment matrix A suitable for compressed sensing, wherein
the plurality of labels is selected from a population of L different labels so that A is a matrix of size L rows by M columns, and
M is greater than L;
obtaining measurements of relative abundances of the L different labels in the sample, represented by a vector o of L rows by 1 column; and
determining relative abundance of up to M different biological molecule types in the sample, represented by a vector x of M rows by 1 column, based on a method of compressed sensing to solve for x by minimizing a penalty based at least in part on a magnitude of a vector given by A x−o.

2. A method as recited in claim 1, wherein:
the plurality of labels is selected from a population of different fluorophores with corresponding different fluorescent wavelengths; and
obtaining measurements of relative abundance of the L different labels in the sample further comprises obtaining measurements of intensity of each of the corresponding fluorescent wavelengths.

3. A method as recited in claim 1, wherein:
the plurality of labels is selected from a population of different isotopes of elements which are not otherwise found in biological organisms and which have ions of different corresponding masses; and
obtaining measurements of relative abundance of the L different labels in the sample further comprises reducing the sample to ions of its constituent elements and obtaining measurements of abundance of each of the corresponding masses in a time of flight mass spectrometer.

4. A method as recited in claim 1, wherein:
each different biological molecule type is a different protein; and
labeling each different biological molecule type in the biological sample with a unique combination of the plurality of labels further comprises
attaching each label in the unique combination to an antibody that binds to the different protein to produce a plurality of labeled antibodies,
contacting the biological sample with the plurality of labeled antibodies for each different protein.

5. A method as recited in claim 4, wherein the biological sample comprises whole cells and each different protein is a different receptor for an outer cell membrane of at least some cells.

6. A method as recited in claim 4, wherein the biological sample comprises permeabilized cells and each different protein is found inside at least some cells.

7. A method as recited in claim 1, wherein the method of compressed sensing comprises selecting abundances for up to M different molecular types by minimizing an order one distance metric designated $l_1$ between computed and measured abundances of the L different labels.

8. A method as recited in claim 1, wherein the method of compressed sensing comprises selecting abundances for up to M different molecular types by minimizing a sum of a first term and an order one distance metric designated $l_1$ of computed abundances of the L different labels, wherein the first term is a parameter $\lambda$ times a computed abundance of the biological molecule.

9. A method as recited in claim 8, wherein a value for the parameter $\lambda$ is chosen to provide agreement with known abundances of the different biological molecule types for a test set.

10. A method as recited in claim 1, wherein the unique combination of labels for each different molecule type is assigned at random.

11. A method as recited in claim 1, wherein the unique combination of labels for each different molecule type is assigned at random with up to y of the L labels, wherein y is less than L.

12. A method as recited in claim 1, wherein the unique combination of labels for each different molecule type is chosen to provide agreement with known abundances of the different biological molecule types for a test set.

13. A method as recited in claim 1, further comprising obtaining the biological sample such that the biological sample includes a number N of the biological molecule types, wherein N is less than about L.

14. A method as recited in claim 1, wherein labeling each different biological molecule type in the biological sample with a unique combination of a plurality of labels further comprises equalizing ratios of each label in each unique combination.

15. A method as recited in claim 1, further comprising
labeling each different biological molecule type in a separate subsample of the sample with a second unique combination of a plurality of labels selected from a population of M different labels;
obtaining second measurements of relative abundances of the M different labels in the sample; and
determining second relative abundance of the M different biological molecule types in the sample based on the second measurements; and
determining adequacy of the unique combination of the plurality of labels selected from the population of L different labels based on comparing the second relative abundances to the relative abundances based on compressed sensing.

16. A method as recited in claim 15, further comprising repeating all steps for N new biological molecule types with a third unique combination of the labels selected from a population of L different labels wherein N is greater than L and a fourth unique combination of a plurality of labels selected from a population of N different labels.

17. An apparatus comprising:
at least one processor; and
at least one memory including one or more sequences of instructions,
the at least one memory and the one or more sequences of instructions configured to, with the at least one processor, cause the apparatus to perform at least the following,
determine a set of L different labels for each of which abundance can be measured;

determine a set of M different biological molecule types to be detected, wherein M is greater than L;

determine an assignment matrix A suitable for compressed sensing that indicates a unique combination of a plurality of labels for each molecule type so that A is a matrix of size L rows by M columns;

cause the different biological molecule types to be physically labeled according to the assignment matrix by presenting data that indicates the assignment matrix;

after presenting data that indicates the assignment matrix, obtain measurements of abundance of labels in a biological sample represented by a vector o of L rows by 1 column, wherein the measurements are based on the assignment matrix; and determine abundances for up to M different molecule types in the biological sample represented by a vector x of M rows by 1 column, based on techniques of compressed sensing to solve for x by minimizing a penalty based at least in part on a magnitude of a vector given by A x–o.

18. An apparatus as recited in claim 17, wherein to determine abundances for up to M different molecule types in the biological sample based on techniques of compressed sensing further comprises to determine abundances for up to M different molecular types by minimizing a sum of a first term and an order one distance metric designated of computed abundances of the L different labels, wherein the first term is a parameter λ times a computed abundance of the biological molecule.

19. An apparatus as recited in claim 18, wherein the at least one memory and the one or more sequences of instructions, with the at least one processor, are further configured to cause the apparatus to determine a value for the parameter λ that provides agreement with known abundances of the different biological molecule types for a test set.

20. An apparatus as recited in claim 17, wherein to determine the assignment matrix that indicates the unique combination of the plurality of labels for each molecule type further comprises to determine the assignment matrix that provides agreement with known abundances of the different biological molecule types for a test set.

21. An apparatus as recited in claim 17, wherein the at least one memory and the one or more sequences of instructions are further configured to perform operating a cell sorter based on the abundances determined for the up to M different molecule types in the biological sample.

22. An apparatus comprising:

means for physically labeling a plurality of M different biological molecule types in a biological sample, each different biological molecule type with a unique combination of a plurality of labels, according to by an assignment matrix A suitable for compressed sensing, wherein each different biological molecule type is selected from a population of M different biological molecules types, the plurality of labels is selected from a population of L different labels so that A is a matrix of size L rows by M columns, and M is greater than L;

means for obtaining measurements of relative abundance of the L different labels in the sample represented by a vector o of L rows by 1 column; and means for determining relative abundance of up to M different molecule types in the sample, represented by a vector x of M rows by 1 column, based on a method of compressed sensing to solve for x by minimizing a penalty based at least in part on a magnitude of a vector given by A x–o.

23. A non-transitory computer-readable medium carrying one or more sequences of instructions, wherein execution of the one or more sequences of instructions by one or more processors causes the one or more processors to perform to:

determine a set of L different labels for each of which abundance can be measured;

determine a set of M different biological molecule types to be detected;

determine an assignment matrix A suitable for compressed sensing that indicates a unique combination of a plurality of labels for each molecule type so that A is a matrix of size L rows by M columns;

cause the different biological molecule types to be physically labeled according to the assignment matrix by presenting data that indicates the assignment matrix;

after presenting data that indicates the assignment matrix, obtain measurements of abundance of labels in a biological sample represented by a vector o of L rows by 1 column, wherein the measurements are based on the assignment matrix; and determine abundances for up to M different molecule types in the biological sample represented by a vector x of M rows by 1 column, based on techniques of compressed sensing to solve for x by minimizing a penalty based at least in part on a magnitude of a vector given by A x–o.

* * * * *